US007223844B2

(12) United States Patent
Dimitrov et al.

(10) Patent No.: US 7,223,844 B2
(45) Date of Patent: May 29, 2007

(54) BROADLY CROSS-REACTIVE NEUTRALIZING ANTIBODIES AGAINST HUMAN IMMUNODEFICIENCY VIRUS SELECTED BY ENV-CD4-CO-RECEPTOR COMPLEXES

(75) Inventors: Dimiter S. Dimitrov, Rockville, MD (US); Maxime Moulard, Auriol (FR); Xiadong Xiao, Frederick, MD (US); Yuuei Shu, Rockville, MD (US); Sanjay K. Phogat, Frederick, MD (US); Mei-Yun Zhang, Frederick, MD (US); Dennis Burton, La Jolla, CA (US)

(73) Assignees: United States of America, Represented by the Secretary, Department of Health and Human Services, Washington, DC (US); Scripps Research Institute, La Jolla, CA (US)

( * ) Notice: Subject to any disclaimer, the term of this patent is extended or adjusted under 35 U.S.C. 154(b) by 0 days.

(21) Appl. No.: 10/492,729

(22) PCT Filed: Oct. 16, 2002

(86) PCT No.: PCT/US02/33165

§ 371 (c)(1),
(2), (4) Date: May 5, 2004

(87) PCT Pub. No.: WO03/033666

PCT Pub. Date: Apr. 24, 2003

(65) Prior Publication Data
US 2004/0259075 A1    Dec. 23, 2004

Related U.S. Application Data

(60) Provisional application No. 60/329,709, filed on Oct. 16, 2001.

(51) Int. Cl.
C07K 16/00    (2006.01)
(52) U.S. Cl. .................. 530/391.1; 530/350; 530/380; 530/386; 530/387.1; 530/388.1; 530/388.15; 530/388.22; 530/388.35; 435/332; 435/334; 435/339.1; 424/142.1; 424/148.1; 424/159.1; 424/160.1; 424/178.1
(58) Field of Classification Search ............. 530/387.3, 530/387.9, 388.1, 388.15, 388.22, 388.35, 530/389.1, 389.4, 391.1, 391.7; 435/455, 435/332, 334, 339.1; 424/141.1, 142.1, 148.1, 424/159.1, 160.1, 178.1
See application file for complete search history.

(56) References Cited

U.S. PATENT DOCUMENTS
5,518,723 A    5/1996 DeVico et al.
5,925,741 A    7/1999 Gershoni
6,030,772 A    2/2000 Devico et al.

FOREIGN PATENT DOCUMENTS
WO    WO 03/095492 A    11/2003

OTHER PUBLICATIONS

Moulard et al. "Broadly cross-reactive HIV-1-neutralizing human monoclonal Fab selected for binding to gp120-CD4-CCR5 complexes" Proceedings of the National Academy of Sciences of the United States of America, vol. 99, No. 10 (May 14, 2002) pp. 6913-6918.*
Mirzabekov et al. "Paramagnetic proteoliposomes containing a pure, native, and oriented seven-transmembrane segment protein, CCR5", Nature Biotechnology, vol. 18 (Jun. 2000), pp. 649-654.*
Golding et al. "Increased association of glycoprotein 120-CD4 with HIV type 1 coreceptors in the presence of complex-enhanced anti-CD4 monoclonal antibodies", AIDS Research and Human Retroviruses. vol. 15, No. 2, (1999), pp. 149-159.*
Burton et al., "Efficient Neutralization of Primary Isolates of HIV-1 by a Recombinant Human Monoclonal Antibody," *Science*, 266, 1024-1027 (1994).
Conley et al., "Neutralization of Divergent Human Immunodeficiency Virus Type 1 Variants and Primary Isolates by IAM-41-2F5, an Anti-gp41 Human Monoclonal Antibody," *Proc. Natl. Acad. Sci. USA*, 91, 3348-3352 (1994).
Dimitrov, "Cell Biology of Virus Entry," *Cell*, 101, 697-702 (2000).
Dimitrov, "Fusin—A Place for HIV-1 and T4 Cells to Meet," *Nat. Med.*, 2 (6), 640-641 (1996).
Hoogenboom et al., "Antibody Phage Display Technology and Its Applications," *Immunotechnology*, 4, 1-20 (1998).
Trkola et al., "Human Monoclonal Antibody 2G12 Defines a Distinctive Neutralization Epitope on the gp120 Glycoprotein of Human Immunodeficiency Virus Type 1," *J. Virol.*, 70 (2), 1100-1108 (1996).
Kilby et al., *Nature Medicine*, 4(11), 1302-1307 (1998).
Kwong et al., *Nature*, 393, 648-659 (1998).
Sattentau et al., *J. of Virology*, 67(12), 7383-7393 (1993).
Wyatt et al., *J. of Virology*, 69(9), 5723-5733 (1995).
Thali et al., *Journal of Virology*, 67, 3978-3988 (1993).
Lapham et al., *Science*, 274, 602-605 (1996).
Xiao et al., *Proc. Natl. Acad. Sci., USA* 95, 7496-7501 (Jun. 1999).

* cited by examiner

*Primary Examiner*—Bruce R. Campell
*Assistant Examiner*—Nicole Kinsey
(74) *Attorney, Agent, or Firm*—Leydig, Voit & Mayer, Ltd.

(57) ABSTRACT

The present invention features antibodies and antibody fragments that specifically bind a CD4-inducible HIV gp120 epitope that is enhanced by binding a co-receptor for HIV, such as CCR5 or CXCR4, and pharmaceutical compositions comprising the antibodies or antibody fragments. The invention also features nucleic acids encoding the antibodies or antibody fragments, pharmaceutical compositions comprising the nucleic acids encoding the antibodies or antibody fragments, vectors comprising the nucleic acids, and cells comprising the vectors. The invention further features methods of identifying antibodies or antibody fragments with broadly neutralizing activity against HIV. The invention also features methods of inhibiting HIV entry into cells and methods of inhibiting replication of HIV in mammals, using the antibodies and nucleic acids of the invention.

27 Claims, 8 Drawing Sheets

X5 Light Chain

| OmpA signal | FR1 |
|---|---|

M K K T A I A I A V A L A G F A T V A Q A A E L V L T Q S P G T L S L A

| | CDR1 | FR2 |
|---|---|---|

G E R A T L S C R A S Q S V S S G S L A W Y Q Q K P G Q A P R L L I Y G A

| CDR2 | | FR3 | |
|---|---|---|---|

S T R A T G I P D R F S G S G S G T D F T L T I G R L E P E D L A V Y Y C Q

| CDR3 | JK | CL |
|---|---|---|

X5 Heavy chain

```
        PelB Signal                              FR1
M K Y L L P T A A A G L L L L A A Q P A M A  E V Q L L E Q S G A E V K K
                                CDR1           FR2
P G S S V Q V S C K A S G G T F S M Y G F N  W V R Q A P G H G L E W M G CDR2                                    FR3
G I I P I F G T S N Y A Q K F R G  R V T F T A D Q A T S T A Y M E L T N L R
                                       CDR3
S D D T A V Y Y C A R  D F G P D W E D G D S Y D G S G R G F F D F  W G Q FR4                                    CH1
G T L V T V S S  A S T K G P S V F P L A P S S K S T S G G T A A L G C L V
                P G

BROADLY CROSS-REACTIVE NEUTRALIZING ANTIBODIES AGAINST HUMAN IMMUNODEFICIENCY VIRUS SELECTED BY ENV-CD4-CO-RECEPTOR COMPLEXES

CROSS-REFERENCE TO RELATED APPLICATIONS

This application is the U.S. national phase of International Patent Application No. PCT/US02/33165, which was filed on Oct. 16, 2002 and which claims the benefit of U.S. Provisional Patent Application No. 60/329,709, which was filed on Oct. 16, 2001.

STATEMENT OF FEDERALLY SPONSORED RESEARCH

This invention was made with government support under Contract No. AI33292 by the National Institutes of Health. The government of the United States of America has certain rights in the invention.

FIELD OF THE INVENTION

This invention generally relates to broadly neutralizing antibodies against Human Immunodeficiency Virus, and methods of making and using the same.

BACKGROUND OF THE INVENTION

The Human Immunodeficiency Virus (HIV) is the causative agent of Acquired Immunodeficiency Syndrome (AIDS). HIV entry into cells involves formation of a complex between the HIV envelope glycoprotein (Env, which consists of a complex containing the HIV glycoproteins gp120 and gp41; gp120-gp41), a cell-surface receptor (CD4), and a cell-surface co-receptor (e.g., the chemokine receptor CCR5 or CXCR4). Binding of Env to CD4 and either co-receptor initiates a series of conformational changes that are the heart of the fusion machinery leading to viral entry into the target cell. Therefore, efforts to develop a vaccine for the prevention and/or treatment of HIV infection have focused upon the development of neutralizing antibodies that specifically bind to Env. However, the extensive variation of Env in the numerous isolates of HIV so far identified presents a major obstacle in designing an effective immunogen for the isolation of antibodies with broadly neutralizing activity against multiple HIV isolates.

Currently there are only three well-characterized monoclonal antibodies (mAbs) with broadly neutralizing activity: the anti-gp120 mAbs b12 (Burton et al. *Science* 266:1024–1027, 1994) and 2G12 (Trkola et al. *J. Virol.* 70:1100–1108, 1996), and the anti-gp41 mAb 2F5 (Conley et al. *Proc. Natl. Acad. Sci. U.S.A.* 91:3348–3352, 1994). Given the ever-increasing number of people infected with HIV, there is a need in the art for additional antibodies with broadly neutralizing activity against HIV, which can be used as passive immunotherapy or passive immunoprophylaxis to treat, ameliorate, inhibit, or prevent HIV infections in individuals who have, or who at risk for developing, such infections. Furthermore, there is a need in the art for new strategies by which to identify and/or isolate such broadly neutralizing anti-HIV antibodies.

SUMMARY OF THE INVENTION

We have discovered that purified complexes containing HIV Env together with the cell-surface HIV receptor CD4 and an HIV co-receptor, e.g., CCR5 or CXCR4, can be used to identify and isolate antibodies, and active fragments thereof, which display broadly neutralizing activity against multiple genetic subtypes of HIV. Such antibodies can be used as inhibitors of HIV infection and for development of HIV vaccines.

In a first aspect, the invention relates to an isolated antibody or antibody fragment that specifically binds a CD4-inducible epitope on Human Immunodeficiency Virus (HIV) Env that is enhanced by the binding of Env to a co-receptor for HIV, wherein the CD4-inducible epitope is distinct from the HIV co-receptor binding site on gp120.

In one embodiment of the first aspect of the invention, the antibody or antibody fragment is selected by virtue of its ability to specifically bind to a CD4-inducible epitope on HIV Env that is enhanced by binding a co-receptor for HIV.

In a second aspect, the invention relates to an isolated antibody or antibody fragment that is selected by virtue of its ability to specifically bind to a CD4-inducible epitope on Human Immunodeficiency Virus (HIV) Env that is enhanced by the binding of Env to a co-receptor for HIV, and wherein the CD4-inducible epitope is distinct from the HIV co-receptor binding site on gp120.

In various embodiments of the first and second aspects of the invention, the epitope can be on gp120, on gp41, or on gp120-gp41 (Env).

In a third aspect, the invention relates to an isolated antibody or antibody fragment that is selected by virtue of its ability to specifically bind to a complex comprising HIV gp120, CD4, and a co-receptor for HIV. In one embodiment of the third aspect of the invention, the complex also comprises gp41.

In various embodiments of the first, second, and third aspects of the invention, the HIV co-receptor can be CCR5 or CXCR4; the isolated antibody or antibody fragment can have broadly neutralizing activity against HIV, e.g., HIV-1; the isolated antibody or antibody fragment can be monoclonal; the isolated antibody or antibody fragment can be human or humanized; and/or the isolated antibody or antibody fragment can be isolated from a phage display library.

In other embodiments of the first, second, and third aspects of the invention, the antibody or antibody fragment can comprise the heavy chain of the Fab fragment X5 (SEQ ID NO: 3), the light chain of the Fab fragment X5 (SEQ ID NO: 2), or both chains of X5.

In still other embodiments of the first, second, and third aspects of the invention, the isolated antibody or antibody fragment can comprise the CDR3 region (SEQ ID NO: 5) of the heavy chain of the Fab fragment X5 and/or the CDR3 region (SEQ ID NO: 8) of the light chain of the Fab fragment X5. The antibody or antibody fragment can also comprise any of the other CDR and/or FR regions found in the heavy or light chain of antibody Fab fragment X5, in any combination.

In yet other embodiments of the first, second, and third aspects of the invention, a fusion polypeptide comprising a heavy chain or light chain of the antibody or antibody fragment can comprise a soluble CD4 (sCD4) domain. Such a polypeptide can further comprise an amino acid sequence corresponding to that of the peptide T20, which is a synthetic peptide derived from the HIV gp41 amino acid sequence.

In a fourth aspect, the invention relates to an isolated polypeptide comprising the heavy chain of antibody Fab fragment X5 (SEQ ID NO: 3).

In a fifth aspect, the invention relates to an isolated polypeptide comprising the light chain of antibody Fab fragment X5 (SEQ ID NO: 2).

In a sixth aspect, the invention relates to an isolated polypeptide comprising the CDR3 region (SEQ ID NO: 5) of the heavy chain of antibody Fab fragment X5.

In a seventh aspect, the invention relates to an isolated polypeptide comprising the CDR3 region (SEQ ID NO: 8) of the light chain of antibody Fab fragment X5.

In an eighth aspect, the invention relates to an isolated polypeptide comprising the CDR3 region (SEQ ID NO: 5) of the heavy chain of antibody Fab fragment X5 and the CDR3 region (SEQ ID NO: 8) of the light chain of antibody Fab fragment X5. For example, the polypeptide can be a single chain antibody or a single chain antibody fragment, such as a single chain variable fragment (ScFv).

In a ninth aspect, the invention relates to an antibody or antibody fragment that is an amino acid sequence variant of the Fab fragment X5, wherein the sequence variant of X5 comprises at least one amino acid substitution in the heavy chain or light chain of X5, wherein the sequence variant of X5 binds a complex comprising gp120, CD4, and an HIV-co-receptor with an affinity that is about equal to or greater than the affinity by which X5 binds the comprising gp120, CD4, and an HIV-co-receptor.

In one embodiment of the ninth aspect of the invention, the sequence variant of X5 has broadly neutralizing activity against HIV-1. In other embodiments, the amino acid substitution is in the CDR3 region of the heavy chain and/or light chain of X5. The amino acid substitution can also be in any other region of the heavy or light chains, e.g., in any of the CDR, FR, or CH1 regions; for example, the amino acid substitution can be in CH1, and the sequence variant of X5 can comprise SEQ ID NO: 11.

In another embodiment of the ninth aspect of the invention, the sequence variant of X5 is selected by virtue of its ability to specifically bind to a complex comprising HIV gp120, CD4, and a co-receptor for HIV. In another embodiment, the sequence variant of X5 is selected by virtue of its ability to specifically bind to a CD4-inducible epitope on HIV Env that is enhanced by binding a co-receptor for HIV.

In a tenth aspect, the invention relates to an isolated polypeptide comprising an amino acid sequence variant of a CDR3 region of antibody Fab fragment X5, wherein an antibody or antibody fragment comprising the amino acid sequence variant of the CDR3 region of X5 binds HIV gp120 with an affinity that is about equal to or greater than to the affinity by which X5 binds gp120. The CDR3 region may be from the heavy chain or the light chain of antibody X5.

In one embodiment of the ninth and tenth aspects of the invention, the amino acid sequence variant is selected by virtue of its equivalent or increased affinity for gp120 relative to the affinity of X5 for gp120.

In an eleventh aspect, the invention relates to an isolated nucleic acid that encodes SEQ ID NO: 3.

In a twelfth aspect, the invention relates to an isolated nucleic acid that encodes SEQ ID NO: 2.

In a thirteenth aspect, the invention relates to an isolated nucleic acid that encodes SEQ ID NO: 5.

In a fourteenth aspect, the invention relates to an isolated nucleic acid that encodes SEQ ID NO: 8.

In a fifteenth aspect, the invention relates to an isolated nucleic acid that encodes an antibody or antibody fragment comprising the CDR3 region (SEQ ID NO: 5) of the heavy chain of antibody Fab fragment X5 and the CDR3 region (SEQ ID. NO: 8) of the light chain of antibody Fab fragment X5.

In a sixteenth aspect, the invention relates to an isolated nucleic acid that encodes an antibody or antibody fragment comprising the heavy chain of antibody Fab fragment X5 (SEQ ID NO: 3) and the light chain of antibody Fab fragment X5 (SEQ ID NO: 2). For example, the isolated nucleic acid can comprise the nucleotide sequence set forth in SEQ ID NO: 4.

In a seventeenth aspect, the invention relates to an isolated vector comprising the isolated nucleic acid of aspects eleven through sixteen above. The vector can be, for example, an expression vector for expression of the peptide or polypeptide encoded by the isolated nucleic acid.

In an eighteenth aspect, the invention relates to an isolated cell comprising the isolated vector of the seventeenth aspect of the invention. The cell can be a prokaryotic cell or a eukaryotic cell.

In a nineteenth aspect, the invention relates to a pharmaceutical composition comprising the isolated antibody or antibody fragment of the first three aspects and the ninth aspect of the invention, and a pharmaceutically acceptable carrier. The pharmaceutical composition can further comprise soluble CD4.

In a twentieth aspect, the invention relates to a pharmaceutical composition comprising a nucleic acid that encodes the isolated antibody or antibody fragment of the first three aspects and the ninth aspect of the invention, and a pharmaceutically acceptable carrier. In one embodiment of the twentieth aspect of the invention, the nucleic acid is within an expression vector.

In a twenty-first aspect, the invention relates to a method of selecting an antibody or antibody fragment with broadly neutralizing activity against HIV, comprising detecting an antibody or antibody fragment that specifically binds a CD4-inducible epitope on HIV Env that is enhanced by the binding of Env to a co-receptor for HIV, wherein the CD4-inducible epitope is distinct from the HIV co-receptor binding site on gp120. For example, the antibody or antibody fragment can be selected by virtue of its binding to a complex comprising HIV gp120, CD4, and a co-receptor for HIV.

In a twenty-second aspect, the invention relates to an antibody produced by the method of the twenty-first aspect of the invention.

In a twenty-third aspect, the invention relates to a method of inhibiting entry of HIV into a cell, comprising administering to the cell an effective amount of an isolated antibody or antibody fragment that specifically binds a CD4-inducible epitope on HIV Env that is enhanced by the binding of Env to a co-receptor for HIV, wherein the CD4-inducible epitope is distinct from the HIV co-receptor binding site on gp120, thereby inhibiting entry of HIV into the cell.

In various embodiments of the twenty-third aspect of the invention, the cell can be any cell susceptible to HIV infection, e.g., but not limited to, a T cell, a B cell, a monocyte, a macrophage, or a microglial cell. In another embodiment of the twenty-third aspect of the invention, the cell is within a mammal that is susceptible to infection by HIV and the isolated antibody or antibody fragment is administered to the mammal.

In a twenty-fourth aspect, the invention relates to a method of inhibiting replication of HIV in a mammal that is susceptible to HIV infection, comprising administering to the mammal an effective amount of an isolated antibody or antibody fragment that specifically binds a CD4-inducible epitope on HIV Env that is enhanced by the binding of Env to a co-receptor for HIV, wherein the CD4-inducible epitope is distinct from the HIV co-receptor binding site on gp120, thereby inhibiting replication of HIV in the mammal.

In various embodiments of the twenty-third and twenty-fourth aspects of the invention, the isolated antibody or antibody fragment is administered to the mammal by administering a nucleic acid encoding the isolated antibody or antibody fragment to the mammal.

In other embodiments of the twenty-third and twenty-fourth aspects of the invention the mammal is a primate, for example, a human or a non-human primate.

In all of the above embodiments of the invention, the HIV can be HIV-1 or HIV-2.

In all of the above embodiments of the invention, the co-receptor can be, e.g., CCR5 or CXCR4.

Additional advantages of the invention will be set forth in part in the description which follows, and in part will be apparent from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention as claimed.

Definitions

In this specification and in the claims which follow, reference will be made to a number of terms which shall be defined to have the following meanings. It is to be understood that the terminology used herein is for the purpose of describing particular embodiments only and is not intended to be limiting.

By "specifically binds", "specifically reacts with", "specifically interacts with", and similar terms is meant that an anti-HIV antibody of the invention physically associates with its target molecule (e.g., gp120 and/or gp41 of HIV Env) to inhibit HIV entry into a cell and/or to inhibit or prevent HIV replication in a mammal. Preferably, the antibody does not substantially physically associate with other molecules.

By a "broadly neutralizing" antibody against HIV, and similar terms, is meant an antibody that can inhibit the activity (e.g., the ability to enter a target cell) of HIV isolates from more than one genetic subtype or clade.

By "CD4-inducible epitope on HIV Env that is distinct from the co-receptor binding site on gp120" is meant that an antibody of the invention does not compete with an HIV co-receptor (e.g., CCR5 or CXCR4) for the co-receptor binding site on gp120. One of ordinary skill in the art will understand how to determine whether an antibody competes with a co-receptor for the co-receptor binding site on Env, using well-known techniques for measuring competition between two molecules for binding to a particular site on a third molecule.

By "selected" is meant that an antibody or antibody fragment of the invention is chosen or isolated from a group or library of candidate antibodies or antibody fragments using a screening assay for choosing or isolating antibodies with a desired characteristic (e.g., the ability to bind a complex comprising HIV gp120, CD4, and a co-receptor for HIV; or the ability to specifically bind a CD4-inducible epitope on HIV Env that is enhanced by the binding of Env to a co-receptor for HIV, wherein the CD4-inducible epitope is distinct from the HIV co-receptor binding site on gp120), as would be understood by one of ordinary skill in the art.

By "CD4-inducible epitope" is meant an antigenic site on HIV Env, gp120, or gp 41, wherein specific binding to the antigenic site by an antibody of the invention is increased or augmented by the binding of CD4 to HIV Env, gp120, or gp41. Preferably the increase is by at least about 2-fold or greater, e.g., at least about: 2-fold, 3-fold, 4-fold, 5-fold, 6-fold, 7-fold, 8-fold, 9-fold, 10-fold, or more. For example, the binding of the anti-HIV antibody X5 (described herein) to gp120 is increased by about 5- to 10-fold when CD4 is present (i.e., when gp120 is bound to CD4, e.g., sCD4).

By "exposure of the epitope is enhanced" or "epitope that is enhanced" is meant that specific binding of an antibody of the invention to its cognate CD4-inducible epitope on HIV Env, gp120, or gp41 is further augmented by the binding of HIV Env, gp120, or gp41 to a co-receptor for HIV (such as the chemokine receptors CCR5 or CXCR4). Preferably the increase is by at least about 1.2-fold or greater, e.g., at least about 1.3-, 1.4-, 1.5-, 1.6-, 1.7-, 1.8-, 1.9-, or 2-fold, or greater.

By "soluble CD4" or "sCD4" or "D1D2" is meant a CD4 molecule, or a fragment thereof, that is in aqueous solution and that can mimic the activity of native membrane-anchored CD4 by altering the conformation of HIV Env, as is understood by those of ordinary skill in the art. One example of a soluble CD4 is the two-domain soluble CD4 (sCD4 or D1D2) described, e.g., in Salzwedel et al. *J. Virol.* 74:326–333, 2000.

By "isolated polypeptide" is meant a polypeptide (or a fragment thereof) that has been separated from the components that naturally accompany it. Typically, the polypeptide is substantially pure when it is at least 60%, by weight, free from the proteins and naturally-occurring organic molecules with which it is naturally associated. Preferably, the polypeptide is at least 75%, more preferably at least 80% or 90%, and most preferably at least 95%, by weight, pure. A substantially pure polypeptide may be obtained, for example, by extraction from a natural source (e.g., a cell), by expression of a recombinant nucleic acid encoding the polypeptide, or by chemically synthesizing the polypeptide. Purity can be measured by any appropriate method, e.g., by column chromatography, polyacrylamide gel electrophoresis, or HPLC analysis.

A protein is substantially free of naturally associated components when it is separated from those contaminants which accompany it in its natural state. Thus, a protein which is chemically synthesized or produced in a cellular system different from the cell from which it naturally originates will be substantially free from its naturally associated components. Accordingly, substantially pure polypeptides not only includes those derived from eukaryotic organisms but also those synthesized in *E. coli* or other prokaryotes.

By "isolated nucleic acid" is meant a nucleic acid molecule that is free of the genes which, in the naturally-occurring genome of the organism from which the DNA of the invention is derived, flank the gene. The term therefore includes, for example, a recombinant DNA which is incorporated into a vector; into an autonomously replicating plasmid or virus; or into the genomic DNA of a prokaryote or eukaryote; or which exists as a separate molecule (e.g., a cDNA or a genomic or cDNA fragment produced by PCR or restriction endonuclease digestion, or an mRNA transcribed from a recombinant DNA template) independent of other sequences. It also includes a recombinant DNA which is part of a hybrid gene encoding additional polypeptide sequence.

By "expression vector" is meant a DNA construct that contains a promoter operably linked to a downstream gene or coding region (e.g., a cDNA or genomic DNA fragment, which encodes a polypeptide or polypeptide fragment). Introduction of the expression vector into the appropriate recipient cell (e.g., a prokaryotic or eukaryotic cell, e.g., a bacterium, yeast, insect cell, or mammalian cell, depending upon the promoter within the expression vector) allows the cell to express mRNA encoded by the expression vector, which is then translated into the encoded polypeptide or polypeptide fragment. Vectors for in vitro transcription/translation are also well-known in the art. An expression vector may be a genetically engineered plasmid, virus, or artificial chromosome derived from, for example, a bacteriophage, adenovirus, retrovirus, poxvirus, or herpesvirus.

By "effective amount" is meant the amount of an anti-HIV antibody of the invention that is useful for treating, partially or completely inhibiting, or preventing an HIV infection in a patient or subject or partially or completely inhibiting entry of HIV into a cell, as described herein. Effective dosages and schedules for administering the antibodies of the invention may be determined empirically, and making such determinations is routine to one of ordinary skill in the art. The skilled artisan will understand that the dosage of anti-HIV antibodies will vary, depending upon, for example, the species of the subject the route of administration, the particular antibody to be used, other drugs being administered, and the age, condition, sex and extent of the disease in the subject. The dosage can be adjusted by the individual physician in the event of any counter-indications. A effective dose of an anti-HIV antibody of the invention generally will range between about 1 μg/kg of body weight and 100 mg/kg of body weight. Examples of such dosage ranges are (but are not limited to), e.g., about 1 μg–100 μg/kg 100 μg–1 mg/kg, 1 mg/kg–10 mg/kg, or 10 mg–100 mg/kg, once week, bi-weekly, daily, or two to four times daily.

DESCRIPTION OF THE DRAWINGS

FIG. 7 is a diagram showing the sequence of the X5 light chain (SEQ ID NO: 2). The OmpA signal sequence, three framework regions (FR1–FR3), three complementarity-determining regions (CDR1–CDR3), kappa chain joining region (Jκ), and light chain constant region (CL) are indicated by heavy horizontal lines above the relevant amino acids.

FIG. 8 is a diagram showing the sequence of the X5 heavy chain (SEQ ID NO: 3). The PelB signal sequence, four framework regions (FR1–FR4), three complementarity-determining regions (CDR1–CDR3), and heavy chain constant region 1 (CH1) are indicated by heavy horizontal lines above the relevant amino acids. The two amino acid positions that are substituted in the X5 sequence variant FabS (described in Example II), are shown below the original X5 heavy chain sequence.

DETAILED DESCRIPTION OF THE INVENTION

Figure 1:
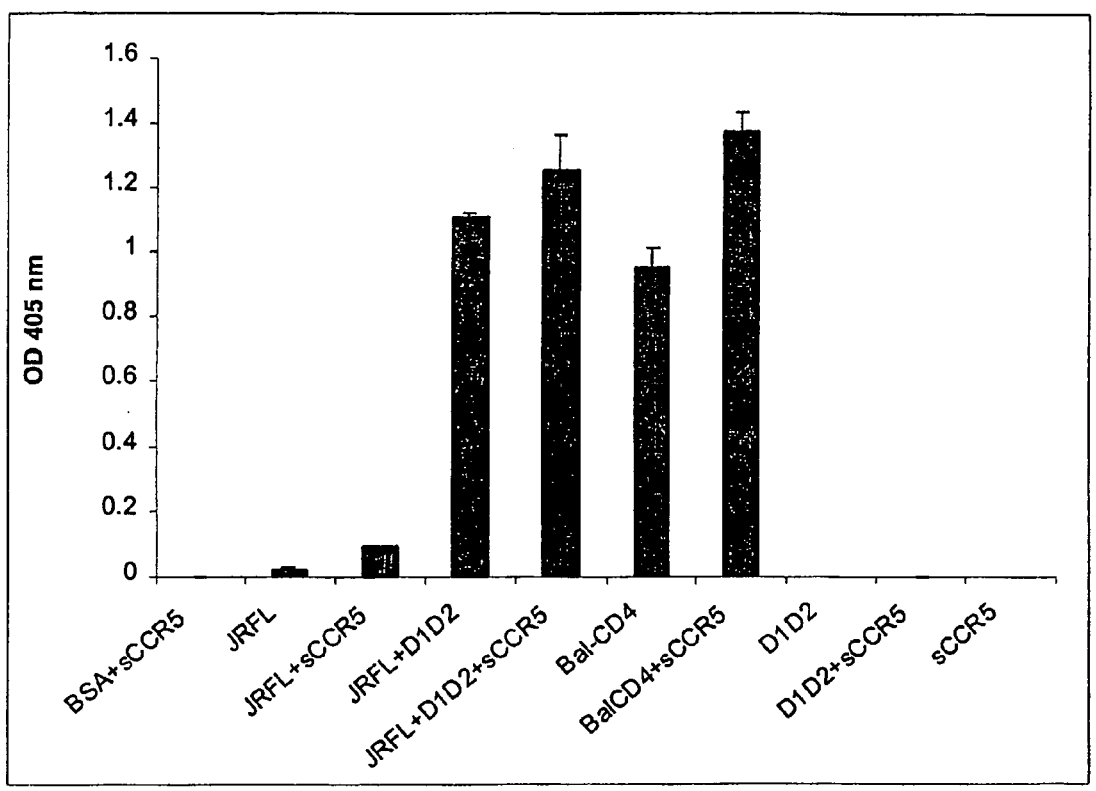
FIG. 1 is a bar graph showing that the X5 epitope is induced by sCD4 and its exposure enhanced by dsCCR5. BSA, gp120$_{JRFL}$, gp120$_{JRFL}$+sCD4, gp120$_{BaL}$-CD4, sCD4 (D1D2) or dsCCR5 (100 ng each in 0.1 ml solution) were coated on an ELISA plate overnight at 4° C. after which the wells were blocked with 4% milk in Tris-buffered saline. Detergent (0.5% Cymal-5)-solubilized CCR5 (dsCCR5) at 100 ng per well containing 0.1 ml buffer was added. In control experiment without dsCCR5 Cymal-5 (0.5%) buffer was added and incubated overnight at 4° C., then X5 Fab was used as primary antibody (Ab) followed by goat anti-human F(ab')$_2$-HRP to detect the signal.

Binding of the HIV envelope glycoprotein (also known as Env or gp120-gp41) to CD4 and the co-receptor CCR5 or CXCR4 initiates a series of conformational changes that are the heart of the fusion machinery leading to viral entry. The elucidation of the nature of the Env conformational changes is not only a clue to the mechanism of HIV-1 entry but also provides new tools for the development of inhibitors and vaccines.

Described herein is a novel approach for the identification of broadly cross-reactive antibodies that neutralize multiple genetic subtypes of HIV. This approach involves the use of purified Env-CD4-co-receptor complexes for screening libraries of antibodies or antibody fragments that specifically bind to receptor-inducible HIV epitopes. Such antibodies can be used for treating, inhibiting, and/or preventing HIV infection by providing passive immunity to treated individuals. Currently there are known only three well characterized monoclonal antibodies with broadly neutralizing activity, and none of these antibodies is directed against a receptor-inducible epitope.

Using this approach, a novel human antibody Fab fragment, denoted "X5", was identified by screening a phage display library, as described in Example I below. The epitope recognized by the X5 antibody is inducible by CD4 and exposure of the epitope is enhanced by the major HIV-1 co-receptor CCR5. The antibody neutralizes R5 and R5X4 viruses, including primary isolates, and to lesser extent, X4 viruses. Sequence variants and antibody fusion proteins based on X5 are also described herein, and will be apparent to those of ordinary skill in the art.

Antibodies

The term "antibodies" is used herein in a broad sense and includes both polyclonal and monoclonal antibodies. In addition to intact immunoglobulin molecules, also included in the term "antibodies" are fragments of immunoglobulin molecules and multimers of immunoglobulin molecules (e.g., diabodies, triabodies, and bi-specific and tri-specific antibodies, as are known in the art; see, e.g., Hudson and Kortt, *J. Immunol. Methods* 231:177–189, 1999), fusion proteins containing an antibody or antibody fragment (e.g., a fusion protein containing a fragment of CD4, e.g., sCD4 (Salzwedel et al. *J. Virol.* 74:326–333, 2000), which are produced using standard molecular biology techniques, single chain antibodies, and human or humanized versions of immunoglobulin molecules or fragments thereof, as long as they are chosen for their ability to broadly neutralize HIV (e.g., multiple genetic subtypes of HIV-1 or HIV-2) by binding a CD4-inducible HIV epitope that is enhanced by binding an HIV co-receptor, as described herein. The antibodies are tested for their desired activity using the in vitro assays described herein, or by analogous methods, after which their in vivo therapeutic and/or prophylactic activities are tested according to known clinical testing methods.

The term "monoclonal antibody" as used herein refers to an antibody or antibody fragment obtained from a substantially homogeneous population of antibodies or antibody fragments, i.e., the individual antibodies within the population are identical except for possible naturally occurring mutations that may be present in a small subset of the antibody molecules. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, as long as they exhibit the desired antagonistic activity (See U.S. Pat. No. 4,816,567 and Morrison et al., *Proc. Natl. Acad. Sci. USA*, 81:6851–6855 (1984)).

Monoclonal antibodies of the invention can be prepared using hybridoma methods, such as those described by Kohler and Milstein, *Nature*, 256:495 (1975). In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro, e.g., using the HIV Env-CD4-co-receptor complexes described herein.

The monoclonal antibodies may also be made by recombinant DNA methods, such as those described in U.S. Pat. No. 4,816,567 (Cabilly et al.). DNA encoding the monoclonal antibodies of the invention can be readily isolated and sequenced using conventional procedures (e.g., by using oligonucleotide probes that are capable of binding specifically to genes encoding the heavy and light chains of murine antibodies). Libraries of antibodies or active antibody fragments can also be generated and screened using phage display techniques, e.g., as described in U.S. Pat. No. 5,804,440 (Burton et al.) and U.S. Pat. No. 6,096,441 (Barbas et al.). Recombinant antibodies, antibody fragments, and fusions and polymers thereof can be expressed in vitro or in prokaryotic cells (e.g., bacteria) or eukaryotic cells (e.g., yeast, insect, or mammalian cells) and further purified, as necessary, using well known methods (see, e.g., Sambrook et al. *Molecular Cloning: a Laboratory Manual*, Cold Spring Harbor Laboratory Press (1989); and Ausubel et al., *Current Protocols in Molecular Biology*, John Wiley & Sons, New York, N.Y., 2001, which is updated quarterly).

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348 published Dec. 22, 1994 and U.S. Pat. No. 4,342,566. Papain digestion of antibodies typically produces two identical antigen binding fragments, called Fab fragments, each with a single antigen binding site, and a residual Fc fragment. Pepsin treatment yields a fragment that has two antigen combining sites and is still capable of cross-linking antigen.

Any antibody or antibody fragment of the invention, whether attached to other sequences or not, can also include insertions, deletions, substitutions, or other selected modifications of particular regions or specific amino acids residues, provided the activity of the antibody or antibody fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody or antibody fragment must possess a bioactive property, such as specific binding to its cognate antigen. Functional or active regions of the antibody or antibody fragment may be identified and/or improved by mutagenesis of a specific region of the protein, followed by expression and testing of the expressed polypeptide. For example, amino acid sequence variants of antibodies or antibody fragments can be generated and those that display equivalent or improved affinity for antigen can be identified using standard techniques and/or those described herein. Methods for generating amino acid sequence variants are readily apparent to a skilled practitioner in the art and can include site-specific mutagenesis or random mutagenesis (e.g., by PCR) of the nucleic acid encoding the antibody or antibody fragment (Zoller, M. J.

*Curr. Opin. Biotechnol.* 3:348–354, 1992). Both naturally occurring and non-naturally occurring amino acids (e.g., artificially-derivatized amino acids) may be used to generate amino acid sequence variants of the antibodies and antibody fragments of the invention.

As used herein, the term "antibody" or "antibodies" can also refer to a human antibody and/or a humanized antibody. Many non-human antibodies (e.g., those derived from mice, rats, or rabbits) are naturally antigenic in humans, and thus can give rise to undesirable immune responses when administered to humans. Therefore, the use of human or humanized antibodies in the methods of the invention serves to lessen the chance that an antibody administered to a human will evoke an undesirable immune response.

Human Antibodies

The human antibodies of the invention can be prepared using any technique. Examples of techniques for human monoclonal antibody production include those described by Cole et al. (*Monoclonal Antibodies and Cancer Therapy*, Alan R. Liss, p. 77, 1985) and by Boerner et al. (*J. Immunol.*, 147(1):86–95, 1991). Human antibodies of the invention (and fragments thereof) can also be produced using phage display libraries (Hoogenboom et al., *J. Mol. Biol.*, 227:381, 1991; Marks et al., *J. Mol. Biol.*, 222:581, 1991; and C. F. Barbas, D. R. Burton, J. K. Scott, G. J. Silverman, *Phage Display: A Laboratory Manual*, Cold Spring Harbor Laboratory Press, Cold Spring Harbor, N.Y., 2001).

The human antibodies of the invention can also be obtained from transgenic animals. For example, transgenic, mutant mice that are capable of producing a full repertoire of human antibodies, in response to immunization, have been described (see, e.g., Jakobovits et al., *Proc. Natl. Acad. Sci. USA*, 90:2551–255 (1993); Jakobovits et al., *Nature*, 362:255–258 (1993); Bruggermann et al., *Year in Immunol.*, 7:33 (1993)). Specifically, the homozygous deletion of the antibody heavy chain joining region (J(H)) gene in these chimeric and germ-line mutant mice results in complete inhibition of endogenous antibody production, and the successful transfer of the human germ-line antibody gene array into such germ-line mutant mice results in the production of human antibodies upon antigen challenge. Antibodies having the desired activity are selected using Env-CD4-coreceptor complexes as described herein.

Humanized Antibodies

Antibody humanization techniques generally involve the use of recombinant DNA technology to manipulate the DNA sequence encoding one or more polypeptide chains of an antibody molecule. Accordingly, a humanized form of a non-human antibody (or a fragment thereof) is a chimeric antibody or antibody chain (or a fragment thereof, such as an Fv, Fab, Fab', or other antigen-binding portion of an antibody) which contains a portion of an antigen binding site from a non-human (donor) antibody integrated into the framework of a human (recipient) antibody.

To generate a humanized antibody, residues from one or more complementarity determining regions (CDRs) of a recipient (human) antibody molecule are replaced by residues from one or more CDRs of a donor (non-human) antibody molecule that is known to have desired antigen binding characteristics (e.g., a certain level of specificity and affinity for the target antigen). In some instances, Fv framework (FR) residues of the human antibody are replaced by corresponding non-human residues. Humanized antibodies may also contain residues which are found neither in the recipient antibody nor in the imported CDR or framework sequences. Generally, a humanized antibody has one or more amino acid residues introduced into it from a source which is non-human. In practice, humanized antibodies are typically human antibodies in which some CDR residues and possibly some FR residues are substituted by residues from analogous sites in rodent antibodies. Humanized antibodies generally contain at least a portion of an antibody constant region (Fc), typically that of a human antibody (Jones et al., *Nature*, 321:522–525 (1986), Reichmann et al., *Nature*, 332:323–327 (1988), and Presta, *Curr. Opin. Struct. Biol.*, 2:593–596 (1992)).

Methods for humanizing non-human antibodies are well known in the art. For example, humanized antibodies can be generated according to the methods of Winter and co-workers (Jones et al., *Nature*, 321:522–525 (1986), Riechmann et al., *Nature*, 332:323–327 (1988), Verhoeyen et al., *Science*, 239:1534–1536 (1988)), by substituting rodent CDRs or CDR sequences for the corresponding sequences of a human antibody. Methods that can be used to produce humanized antibodies are also described in U.S. Pat. No. 4,816,567 (Cabilly et al.), U.S. Pat. No. 5,565,332 (Hoogenboom et al.), U.S. Pat. No. 5,721,367 (Kay et al.), U.S. Pat. No. 5,837,243 (Deo et al.), U.S. Pat. No. 5,939,598 (Kucherlapati et al.), U.S. Pat. No. 6,130,364 (Jakobovits et al.), and U.S. Pat. No. 6,180,377 (Morgan et al.).

Administration of Antibodies

Antibodies of the invention are preferably administered to a subject in a pharmaceutically acceptable carrier. Suitable carriers and their formulations are described in *Remington: The Science and Practice of Pharmacy* (19th ed.) ed. A. R. Gennaro, Mack Publishing Company, Easton, Pa. 1995. Typically, an appropriate amount of a pharmaceutically acceptable salt is used in the formulation to render the formulation isotonic. Examples of the pharmaceutically acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of antibody being administered.

The antibodies can be administered to the subject, patient, or cell by injection (e.g., but not limited to, intravenous, intraperitoneal, intradermal, subcutaneous, intramuscular), or by other methods such as infusion that ensure its delivery to the bloodstream in an effective form. Local or intravenous injection is preferred.

Effective dosages and schedules for administering the antibodies may be determined empirically, and making such determinations is within the skill in the art. Those skilled in the art will understand that the dosage of antibodies that must be administered will vary depending on, for example, the subject that will receive the antibody, the route of administration, the particular type of antibody used and other drugs being administered. Guidance in selecting appropriate doses for antibodies is found in the literature on therapeutic uses of antibodies, e.g., *Handbook of Monoclonal Antibodies*, Ferrone et al., eds., Noges Publications, Park Ridge, N.J., (1985) ch. 22 and pp. 303–357; Smith et al., *Antibodies in Human Diagnosis and Therapy*, Haber et al., eds., Raven Press, New York (1977) pp. 365–389. A typical daily dosage of the antibody used alone might range from about 1 µg/kg to up to 100 mg/kg of body weight or more per day, depending on the factors mentioned above.

Following administration of an antibody for treating, inhibiting, or preventing an HIV infection, the efficacy of the therapeutic antibody can be assessed in various ways well known to the skilled practitioner. For instance, one of ordinary skill in the art will understand that an antibody of the invention is efficacious in treating or inhibiting an HIV infection in a subject by observing that the antibody reduces viral load or delays or prevents a further increase in viral load. Viral loads can be measured by methods that are known in the art, for example, using polymerase chain reaction assays to detect the presence of HIV nucleic acid or antibody assays to detect the presence of HIV protein in a sample (e.g., but not limited to, blood or another body fluid) from a subject or patient, or by measuring the level of circulating anti-HIV antibodies in the patient. Efficacy of the antibody treatment may also be determined by measuring the number of CD4+ T cells in the HIV-infected subject. An antibody treatment that delays or inhibits an initial or further decrease in CD4+ T cells in an HIV-positive subject or patient, or that results in an increase in the number of CD4+ T cells in the HIV-positive subject, is an efficacious antibody treatment.

The broadly-neutralizing antibodies of the invention can also be administered prophylactically to patients or subjects who are at risk for being exposed to HIV or who have been newly exposed to HIV. Such patients include, but are not limited to, healthcare workers; fetuses, neonates, or infants (e.g., nursing infants) whose mothers are infected or at risk for being infected; intravenous drug users; recipients of blood transfusions, blood products, or transplantation tissue; and other individuals who have been exposed to a body fluid that contains or may contain HIV.

In subjects who have been newly exposed to HIV but who have not yet displayed the presence of the virus (as measured by PCR or other assays for detecting the virus) in blood or other body fluid, efficacious treatment with an antibody of the invention partially or completely inhibits or delays the appearance of the virus or minimizes the level of the virus in the blood or other body fluid of the exposed individual.

Nucleic Acid Approaches for Antibody Delivery

The broadly neutralizing anti-HIV antibodies and antibody fragments of the invention can also be administered to patients or subjects as a nucleic acid preparation (e.g., DNA or RNA) that encodes the antibody or antibody fragment, such that the patient's or subject's own cells take up the nucleic acid and produce and secrete the encoded antibody or antibody fragment, thereby treating, inhibiting, or preventing HIV infection.

Nucleic Acid Delivery

In the methods described above which include the administration and uptake of exogenous DNA into the cells of a subject (i.e., gene transduction or transfection), the nucleic acids of the present invention can be in the form of free DNA or RNA, or the nucleic acids can be in a vector for delivering the nucleic acids to a cell and expressing the encoded polypeptide within a cell, whereby the antibody-encoding DNA fragment is under the transcriptional regulation of a promoter, as well as an other necessary and/or desirable components to regulate and/or enhance transcription and/or stability of the mRNA and to regulate and/or enhance translation of the encoded polypeptide, as would be well understood by one of ordinary skill in the art. The vector can be a commercially available preparation, such as a plasmid or an adenovirus vector (Quantum Biotechnologies, Inc. (Laval, Quebec, Canada).

Delivery of the nucleic acid or vector to cells can be via a variety of mechanisms. As one example, delivery can be via a liposome, using commercially available liposome preparations such as LIPOFECTIN, LIPOFECTAMINE (GIBCO-BRL, Inc., Gaithersburg, Md.), SUPERFECT (Qiagen, Inc. Hilden, Germany), and TRANSFECTAM (Promega Biotec, Inc., Madison, Wis.), as well as other liposomes developed according to procedures standard in the art. Delivery can also be by injection (e.g., but not limited to, intravenous or intramuscular) of naked DNA, e.g., in a plasmid or viral vector. In addition, the nucleic acid or vector of this invention can be delivered in vivo by electroporation, the technology for which is available from Genetronics, Inc. (San Diego, Calif.) as well as by means of a SONOPORATION machine (ImaRx Pharmaceutical Corp., Tucson, Ariz.).

As one example, vector delivery can be via a viral system, such as a retroviral vector system which can package a recombinant retroviral genome (see e.g., Pastan et al., *Proc. Natl. Acad. Sci. U.S.A.* 85:4486, 1988; Miller et al., *Mol. Cell. Biol.* 6:2895, 1986). The recombinant retrovirus can then be used to infect and thereby deliver to the infected cells nucleic acid encoding a broadly neutralizing antibody (or active fragment thereof) of the invention. The exact method of introducing the altered nucleic acid into mammalian cells is, of course, not limited to the use of retroviral vectors. Other techniques are widely available for this procedure including the use of adenoviral vectors (Mitani et al., *Hum. Gene Ther.* 5:941–948, 1994), adeno-associated viral (AAV) vectors (Goodman et al., *Blood* 84:1492–1500, 1994), lentiviral vectors (Naidini et al., *Science* 272:263–267, 1996), pseudotyped retroviral vectors (Agrawal et al., *Exper. Hematol.* 24:738–747, 1996). Physical transduction techniques can also be used, such as liposome delivery and receptor-mediated and other endocytosis mechanisms (see, for example, Schwartzenberger et al., *Blood* 87:472–478, 1996). This invention can be used in conjunction with any of these or other commonly used gene transfer methods.

For example, if the antibody-encoding nucleic acid of the invention is delivered to the cells of a subject in an adenovirus vector, the dosage for administration of adenovirus to humans can range from about $10^7$ to $10^9$ plaque forming units (pfu) per injection but can be as high as $10^{12}$ pfu per injection (Crystal, *Hum. Gene Ther.* 8:985–1001, 1997; Alvarez and Curiel, *Hum. Gene Ther.* 8:597–613, 1997). A subject can receive a single injection, or, if additional injections are necessary, they can be repeated at six month intervals (or other appropriate time intervals, as determined by the skilled practitioner) for an indefinite period and/or until the efficacy of the treatment has been established.

Parenteral administration of the nucleic acid or vector of the present invention, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein. For additional discussion of suitable formulations and various routes of administration of therapeutic compounds, see, e.g., *Remington: The Science and Practice of Pharmacy* (19th ed.) ed. A. R. Gennaro, Mack Publishing Company, Easton, Pa. 1995.

The present invention is more particularly described in the following examples, which are intended as illustrative only, since numerous modifications and variations therein will be apparent to those of ordinary skill in the art.

EXAMPLE I

Identification of X5, an Fab Fragment that has Broadly Neutralizing Activity Against HIV-1

A) Materials and Methods

Cells, viruses, plasmids, soluble CD4, gp120, gp140 and mAbs. 3T3 cells expressing CD4 and CCR5 were gift from D. Littman (New York University, NY, N.Y.). Cf2Th cells expressing high amounts of CCR5 were gift from J. Sodroski (Dana Farber Institute, Boston, Mass.); the parental cells was purchased from ATCC and used as negative control. The stable cell line TF228 expressing LAI Env was a gift from Z. Jonak (SmithKline Beechman Pharmaceuticals, Philadelphia, Pa.) through R. Blumenthal (NCI-Frederick, Frederick, Md.). Recombinant vaccinia viruses used for the reporter gene fusion assay were described previously (Nussbaum et al. *J. Virol.* 68:5411–5422, 1994). Plasmids expressing various Envs were obtained through the NIH AIDS Research and Reference Reagent Program or were gift from M. A. Martin (NIAID, Bethesda, Md.). Two-domain soluble CD4 (sCD4 or D1D2) (see e.g., Salzwedel et al. *J. Virol.* 74:326–333, 2000) was a gift from E. Berger (NIAID, Bethesda, Md.). Purified gp120$_{89.6}$ and gp140$_{89.6}$ were produced by recombinant vaccinia virus (gift of R. Doms, University of Pennsylvania, Philadelphia, Pa.) with a combination of lentil lectin affinity chromatography and size exclusion chromatography. Recombinant gp120$_{JRFL}$ was a gift from A. Schultz and N. Miller (NIAD, Bethesda, Md.). The fusion protein gp120$_{Bal}$-CD4 (Fouts et al. *J. Virol.* 74:11427–11436, 2000) was a gift from T. Fouts (Institute of Human Virology, Baltimore, Md.). The anti-CD4 polyclonal antibody T4–4 was obtained through the AIDS Research and Reference Reagent Program from R. Sweet (SmithKline Beechman Pharmaceuticals, Philadelphia, Pa.). The anti-gp120 mAbs 17b, 48d, 23e and 21c were gift from J. Robinson (Tulane University Medical Center, New Orleans, La.). The anti-CCR5 mAb 5C7 was a gift from L. Wu (Millenium Pharmaceuticals, Cambridge, Mass.). The goat polyclonal anti-CCR5 antibody CKR5(C20) was purchased from Santa Cruz Biotechnology, Inc. (Santa Cruz, Calif.).

Production, purification and quantification of gp120-CD4-CCR5 complexes. NIH 3T3 transfectants ($10^9$ in 100 ml) expressing high amounts of CD4 and CCR5 were washed twice with cold (4° C.) phosphate-buffered saline (PBS) then pelleted by centrifugation and resuspended in 100 ml lysis buffer (1% Brij 97, 5 mM iodoacetamide, added immediately before use, 150 mM NaCl, 20 mM Tris (pH 8.2), 20 mM EDTA, and protease inhibitors) at 4° C. for 40 min with gentle mixing. An anti-CCR5 antibody at 2 µg/ml was added to the cell suspension and incubated with gentle mixing for 4 hours at 4° C. The nuclei were pelleted by centrifugation at 14,000 rpm for 25 min in a refrigerated centrifuge. Protein G-Sepharose beads (Sigma, St. Louis, Mo.) (1 ml) prewashed with PBS were added to the cell lysate and incubated at 4° C. for 14 hours. The beads were then washed five times with 100 ml of ice cold lysis buffer and incubated with JRFL gp120 at 5 µg/ml in 20 ml lysis buffer for 1 hour at 4° C. They were again washed five times with 100 cold lysis buffer, incubated with 1% formaldehyde overnight, washed twice with cold lysis buffer and used. They contained approximately 0.01 mg CD4 and 0.02 mg gp120, as quantified by calibrating amounts of soluble CD4 and gp120. For quantification of CD4 and gp120 two duplicated samples each containing 0.1% of the total amount of bead-associated gp120-CD4-CCR5 complexes were used. They were eluted by adding 4× sample buffer for SDS-PAGE gel and kept overnight at 37° C. They were run on a 10% SDS-PAGE gel simultaneously with calibrating amounts (1, 3, 10, 30, 100 ng) of soluble four-domain CD4 (sCD4) (see, e.g., Deen et al. *Nature* 331:82–84, 1988) or gp120 and were electrophoretically transferred to nitrocellulose membranes. The membranes were blocked with 20 mM tris-HCl (pH 7.6) buffer containing 140 mM NaCl, 0.1% Tween-20 and 5% nonfat powdered milk. For Western blotting these membranes were incubated with anti-CD4 or anti-gp120 antibodies, then washed and incubated with horseradish peroxidase (HRP)-conjugated secondary antibodies. They were developed by using the supersignal chemiluminescent substrate from Pierce (Rockford, Ill.). The images were acquired by a BioRad phosphoimager (BioRad, Hercules, Calif.). The signal from the calibrating molecules was integrated for each band and plotted in a calibration curve for the signal vs. amount dependence. The amounts of CD4 and gp120 were then calculated by interpolation using the calibration curve.

Screening of the phage display library. A phage library (IgG1k) from a seropositive individual with a relatively high cross-clade neutralizing antibody titer (FDA2), constructed as described (Burton et al. *Proc. Natl. Acad. Sci. USA* 88:10134–10137, 1991; and C. F. Barbas, D. R. Burton, J. K. Scott, G. J. Silverman, *Phage Display: A Laboratory Manual*, Cold Spring Harbor Laboratory Press, Cold Spring Harbor, N.Y., 2001) was used. Phages (50 µl) were preadsorbed on protein G beads in PBS for 1 h at 37° C. Unbound phages were recovered by centrifugation (1500 rpm for 5 min at 4° C.) and then incubated with protein G beads associated with gp120-CD4-CCR5 complexes for 2 hours at 4° C. under gentle agitation. Beads were washed 10 times with PBS containing 0.5% Tween.

Phages were eluted from the beads by incubation with 50 µl 0.1M HCl-glycine (pH 2.2) solution containing BSA at 1 mg/ml for 10 min at room temperature. The solution was neutralized with 3 µl of 2M TRIS-base. XL1-Blue *E. coli* cells were reinfected and panning repeated for total of 5 rounds of panning.

Preparation of soluble Fab fragments. Phagemid DNA was isolated and digested with Spe I and Nhe I to remove the gene III fragment and self-religated as described elsewhere (Barbas et al. *Proc. Natl. Acad. Sci. US.A.* 88:7978–7982, 1991). The Δgene III-phagemid library was used to transform XL1-Blue *E. coli* cells to produce clones secreting Fab fragments. 60 such clones were grown up and the corresponding Fabs were obtained by lysing the cell pellet. Cells were frozen in a dry ice-ethanol bath for 5 min followed by thawing in a 37° C. water bath. This process was repeated four times and the cell debris were pelleted by centrifugation at 15,000 rpm for 15 minutes at 4° C.

ELISA analysis of Fab supernatants. ELISA wells were coated overnight at 4° C. with 50 µl of gp120 (10 µg/ml in PBS), blocked in 100 µl of 3% BSA/PBS for 1 hour at RT. After 5 washes with 0.05% Tween20/PBS (Washing Buffer, WB), wells were incubated with 50 µl Fab supernatants for 1 hour at RT. After 10 washes with WB, 50 µl of a 1:1000 dilution of alkaline phosphatase-conjugated goat anti-human IgG F(ab')$_2$ was added and incubated for 1 hour at RT. Following 10 washes with WB, the assay was developed with p-nitrophenyl phosphate substrate (Sigma, St. Louis, Mo.) and monitored at 405 nm. Heavy chains from positive clones were sequenced using the SeqGz primer (5'-GAAG-TAGTCCTTGACCAG-3'; SEQ ID NO: 1).

Production and purification of Fab. The selected phage was amplified and purified by standard methods (see C. F. Barbas, D. R. Burton, J. K. Scott, G. J. Silverman, *Phage Display: A Laboratory Manual*, Cold Spring Harbor Laboratory Press, Cold Spring Harbor, N.Y., 2001). Protein G columns were used for purification.

Production and purification of detergent solubilized CCR5 (dsCCR5). DsCCR5 was produced by a methodology adapted from that described previously (Mirzabekov et al. *J. Biol. Chem.* 274:28745–28750, 1999).

Cell-cell fusion inhibition assay. The gene reporter cell-cell fusion assay was previously described (Nussbaum et al. *J. Virol.* 68:5411–5422, 1994). Briefly, recombinant vaccinia viruses at multiplicity of infection 10 were used to infect the target (vCB21R) and effector cells (vTF 7.3 plus virus expressing the HIV-1 Env). The β-gal fusion assay was performed two hours after mixing the cells. The extent of fusion was quantitated calorimetrically. Fusion induced by sCD4 was performed by incubation of $10^5$ effector cells expressing the Env with sCD4 (1 ug/ml) at 37° C. for 30 min before mixing with the target cells (Salzwedel et al. *J. Virol.* 74:326–333, 2000). The inhibitory effect of X5 was evaluated by mixing the effector cells with X5 for 30 min at 37° C. and then performing the fusion assay.

HIV neutralization assay. Virus neutralization assays were performed by using infection with a luciferase reporter HIV-1 Env pseudotyping system (Connor et al. *Virology* 206:935–944, 1995). Viral stocks were prepared by transfecting 293T cells with plasmids encoding the luciferase virus backbone (pNL-Luc-ER) and Env from various HIV strains. The resulting supernatant was clarified by centrifugation for 10 min at 2,000 rpm in a Sorvall RT-7 centrifuge (RTH-750 rotor), passed through a 45-um pore size sterile filter (Millipore, Bedford, Mass.) and used or stored at −80° C. The virus was pre-incubated with various concentrations of X5 (0.1, 1.0, 10.0, 50, and 80 or 100 ug/ml) for 30 min at 37° C. Cells were then infected with 50 µl of virus preparation for 4 h at 37° C., then fresh media was added and incubation was continued for 48 h. Cells were then washed with PBS and lysed with luciferase assay buffer (Promega, Madison, Wis.). Luciferase activity was determined by adding 50 µl of freshly prepared luciferase assay substrate to 50 µl of cell lysate and measuring the intensity of chemiluminescence in a LumiCount microplate luminometer (Turner Designs, Sunnyvale, Calif.). All experiments were performed at least in triplicate and the results expressed as relative light units (RLU) per second.

ELISA binding assay. The assay used for binding is a modified ELISA type assay. Briefly, gp120 or sCD4-gp120 was non-specifically attached to the bottom of 96-well plates by incubation of 0.1 ml solution containing 100 ng of the protein at 4° C. overnight. Plates were then treated with 4% non-fat milk (Biorad) in order to prevent nonspecific binding. The plates were washed with TBS containing 0.1% Tween-20; dsCCR5 in Cymal lysis buffer (1% Cymal, 100 mM $(NH_4)_2SO_4$, 20 mM Tris, 10% glycerol) was then added and incubated at 4° C. overnight. Unbound molecules of dsCCR5 were washed and X5 was added. After washing bound X5 was detected by anti-human IgG.

The antibody competition experiment was performed by using a mixture of the competing Ab (at different concentrations) with 0.5 ug/ml biotinylated X5 instead of X5 alone following the procedure as described above. Biotinylated proteins were prepared by incubation with 2 mM biotin (prepared from solid NHS-LS-Biotin (Pierce, Calif.) dissolved at 200 mM in DMSO as stock solution) on wet ice for 1 h. The biotinylation was quenched with 20 mM glycine on ice for 15 min. Binding of biotinylated X5 was detected using streptavidin-HRP secondary antibody.

Flow cytometry. Cells (typically 0.5×$10^6$) were incubated for 1 h on ice with the antigen specific antibodies. They were washed, and incubated for another hour on ice with rabbit IgG (10 µg/ml) (Sigma, St. Louis, Mo.) to improve the specificity, then washed and incubated for 1 h with an anti-mouse phycoerythrin-conjugated polyclonal antibody (Sigma). The cells were washed and fixed with paraformaldehyde on ice for 10 min. The flow cytometry measurements were performed with FACSCalibur (Becton Dickinson, San Jose, Calif.).

Binding of Env-specific antibodies to HIV-1-infected cells. The T-cell line H9 (a gift from Q.Sattentau and supplied by the MRC AIDS Reagent Project) was grown in RPMI 1640 supplemented with 10% fetal calf serum. H9 cells were infected with the HIV-1 TCLA X4 MN isolate (obtained through the AIDS Research and Reference Reagent Program from R. Gallo) for 10 days to achieve high level of Env expression as detected by gp120-specific mAbs and flow cytometry (see above). Then the antibodies were added at various concentrations, the cells were washed twice, and the bound human antibodies detected using anti-human IgG by flow cytometry as described above.

B) Results

Selection of a phage (X5) with high affinity to gp120-CD4-CCR5 complexes. For panning we used complexes containing about 0.01 mg CD4 and 0.02 mg JRFL gp120. The amount of CCR5 was not determined precisely but was about 0.01 mg as found by comparison of CCR5 Western blots of known amounts of detergent-solubilized CCR5. After 5 rounds of panning one phage was selected. This phage, denoted X5, was amplified. X5 exhibited binding activity to protein G cross-linked to Sepharose beads with an affinity (equilibrium dissociation constant) of 15 nM. Phage-displayed X5 had 15-fold lower effective affinity (1.4 nM) for protein G beads than for the gp120-CD4-CCR5 complex (0.09 nm). The X5 Fab was purified by using protein G columns.

Figure 2:
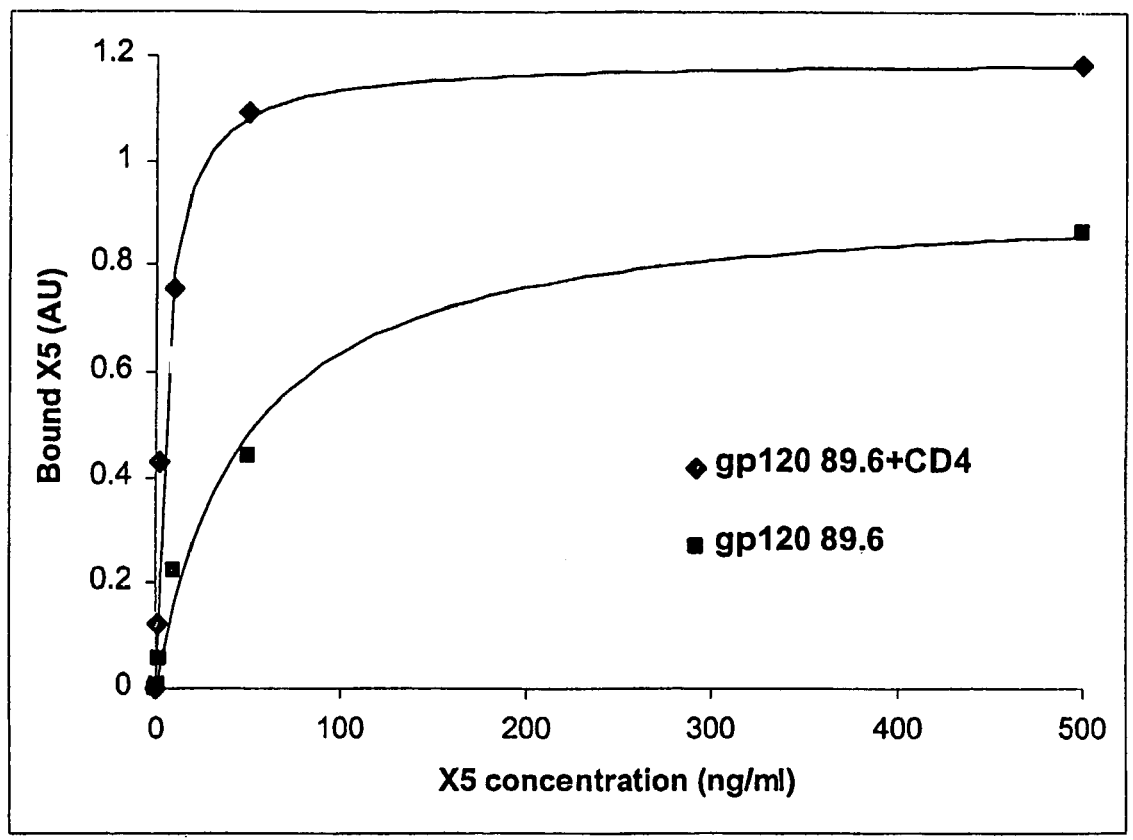
FIG. 2 is a diagram showing binding isotherms of X5 to gp120 and gp120-sCD4. Experimental data for gp120$_{89.6}$ and sCD4-gp120$_{89.6}$ obtained as described for FIG. 1 were analyzed by fitting them to an equation describing the Langmuir adsorption isotherm (B/B$_{max}$=X5/(K$_d$+X5), where B is the amount of bound X5, B$_{max}$ is the maximal amount of bound X5, X5 is its bulk concentration and K$_d$ is the equilibrium dissociation constant (affinity is the inverse of K$_d$). The continuous lines represent fitting of the data for X5 binding to gp120$_{89.6}$ (lower curve) and sCD4-gp120$_{89.6}$ (upper curve) with K$_d$ equal to 9.3 nM and 1.0 nM, respectively.
Figure 3:
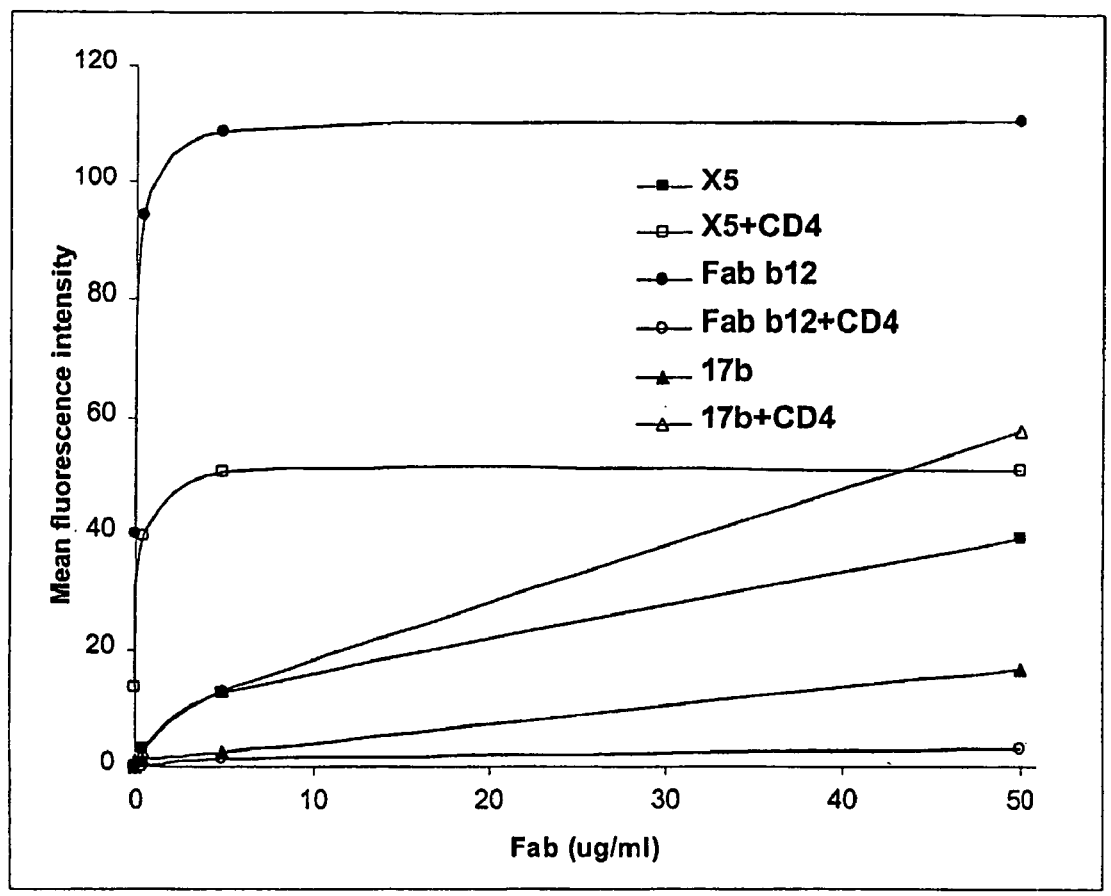
FIG. 3 is a graph showing binding of antibodies X5, b12, and 17b to cell surface-associated functional oligomeric gp120-gp41. The T-cell line H9 was infected with the HIV-1 TCLA X4 MN isolate for 10 days. At this time post-infection there was no detectable CD4 remaining at the cell surface, and no syncytium formation in the culture, but strong Env expression was detected using gp120-specific mAbs and flow cytometry. H9 cells were pre-incubated with sCD4 (20 μg/ml) or buffer alone for 1 h at RT, then incubated with X5 Fab, the anti-CD4i mAb 17b or the anti-CD4BS Fab IgG1b12 at various concentrations. The amount of bound antibodies was measured by flow cytometry.

Binding of X5 to a CD4-inducible epitope on gp120 that is enhanced by dsCCR5. To find whether the Fab of the selected phage was able to bind gp120 and its complexes with CD4 and CCR5 we used an ELISA-type of assay. X5 bound gp120 from several isolates and its binding was increased 5–10-fold after binding of sCD4 (D1D2) to gp120 (FIGS. 1 and 2). The affinity of binding (equilibrium dissociation constants) to $gp120_{89.6}$ and $sCD4-gp120_{89.6}$ complexes was 9.4 nM and 1 nM (FIG. 2), and for JRFL-10 and 2 nM, respectively (FIG. 1). Binding of dsCCR5 further enhanced the X5 epitope exposure by 30–60% (FIG. 1). Similar affinities were observed for binding to oligomeric, fusion-active $gp120-gp41_{MN}$ expressed at the surface of chronically infected H9 cells (FIG. 3). For this experimental system the X5 affinity in presence of sCD4 was comparable to that of CD4bs-specific mAb IgG1b12 in the absence of sCD4 and several fold higher than the affinity of 17b which was previously reported to exhibit an increased affinity to the gp120-CD4 complex (Thali et al. *J. Virol.* 67:3978–3988, 1993). The affinity of X5 for the $gp120_{JRFL}$-sCD4-CCR5 complex used for the X5 selection was 1 nM and the effective affinity of phage-displayed X5 for the $gp120_{JRFL}$-sCD4-CCR5 complex was 0.09 nM. Thus X5 exhibit the highest affinity to the gp120-sCD4 complex among known antibodies to CD4-inducible epitopes. The affinity was not significantly dependent on the tropism of the Envs.

Recombinant gp120 and gp140 from several primary isolates (a gift from C. Broder) behaved similarly. In all (92UG037.8 (Clade A, R5); 92HT593.1 (Clade B, R5 X4); 93ZR001.3 (Clade D, R5 X4) and 89.6) cases binding to gp120 was higher than binding to gp140 suggesting effects of gp41 or/and oligomerization. Therefore, the X5 epitope is a conserved conformational epitope that is induced by CD4 and enhanced by CCR5. This is the first example of an epitope for which exposure is enhanced by CCR5. These results suggest the existence of a very early intermediate in the HIV-1 entry process that is induced by receptor molecules.

Figure 4:
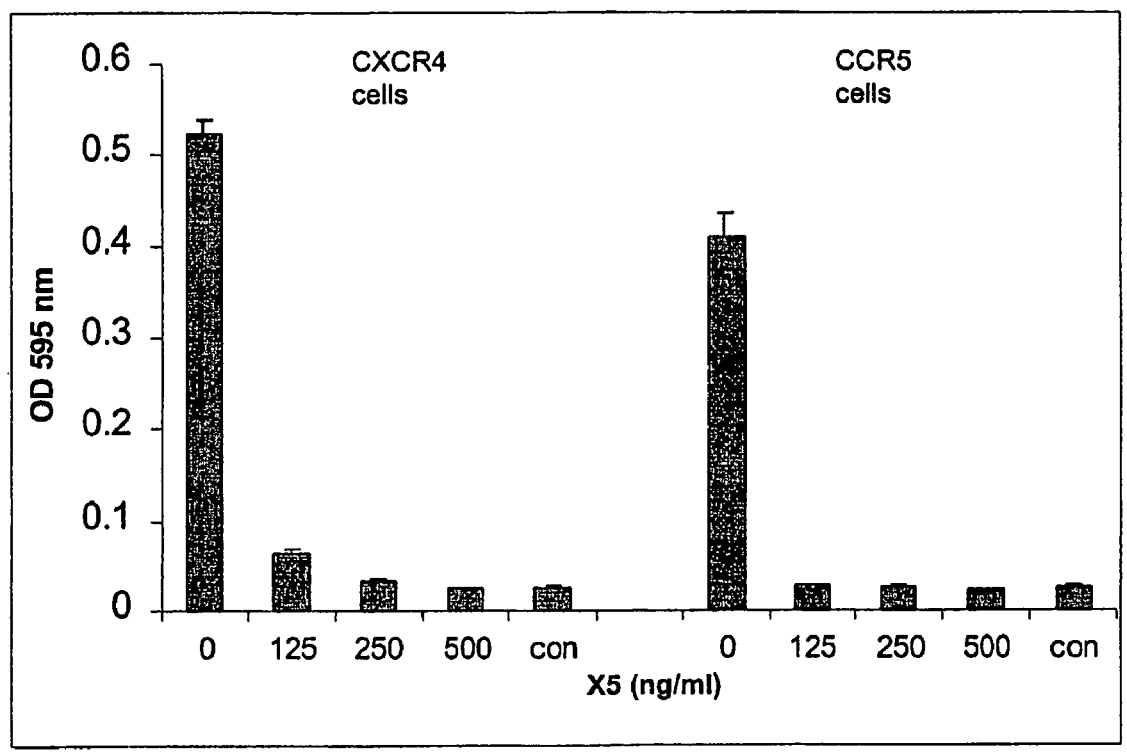
FIG. 4 is a bar graph showing inhibition of sCD4-induced fusion by X5. Fusion between 293 cells, expressing CCR5 or CXCR4 after infection with recombinant vaccinia viruses (PM1107 or DM1107, respectively), and 293 cells, expressing HIV-1$_{89.6}$Env after infection with recombinant vaccinia virus, induced by soluble CD4, was measured by the beta-galactosidase assay. The Env-expressing cells were mixed with sCD4 (1 ug/ml) and X5 (0, 125, 250, 500 ng/ml) for 30 min at 37° C. In a control experiment (con) no sCD4 was added. These cells were mixed with the cells expressing receptor molecules at a ratio of 1:1 (total number of cells equal to 2×105 in 96-well plate format). Fusion was allowed to proceed for 2 h at 37° C. and quantitated by a colorimetric assay which measures the optical density at 595 nm (OD$_{595}$).
Figure 5:
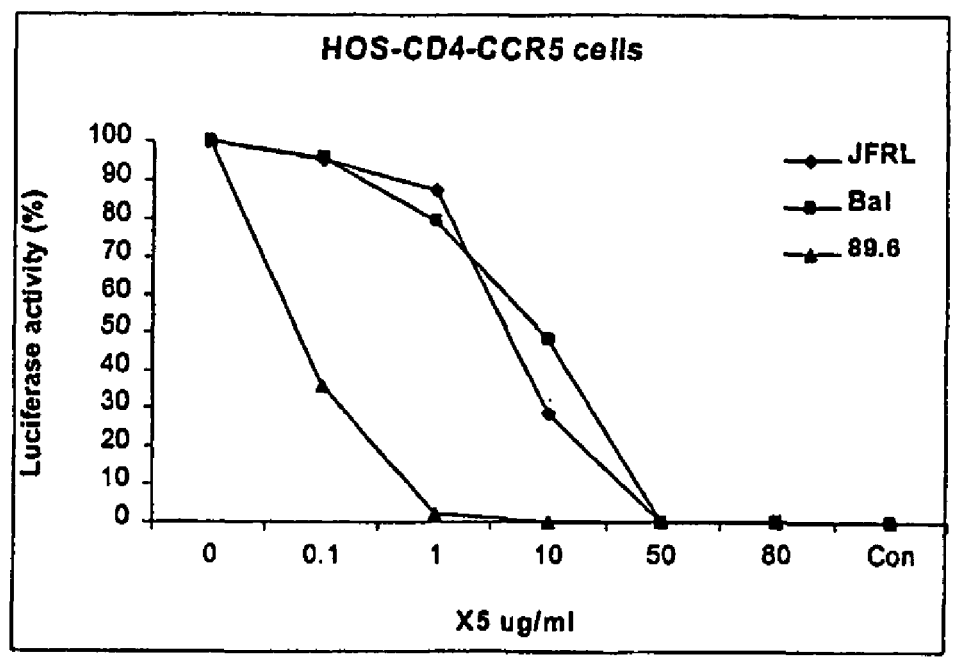
FIGS. 5A and 5B are graphs showing neutralization of HIV infection by X5. Infection of HOS CD4.CXCR4 or HOS CD4.CCR5 cells by pseudotyped HIV-1$_{NL4-3}$ was monitored by a reporter gene assay performed as described in the Materials and Methods section of Example I.
Figure 5:
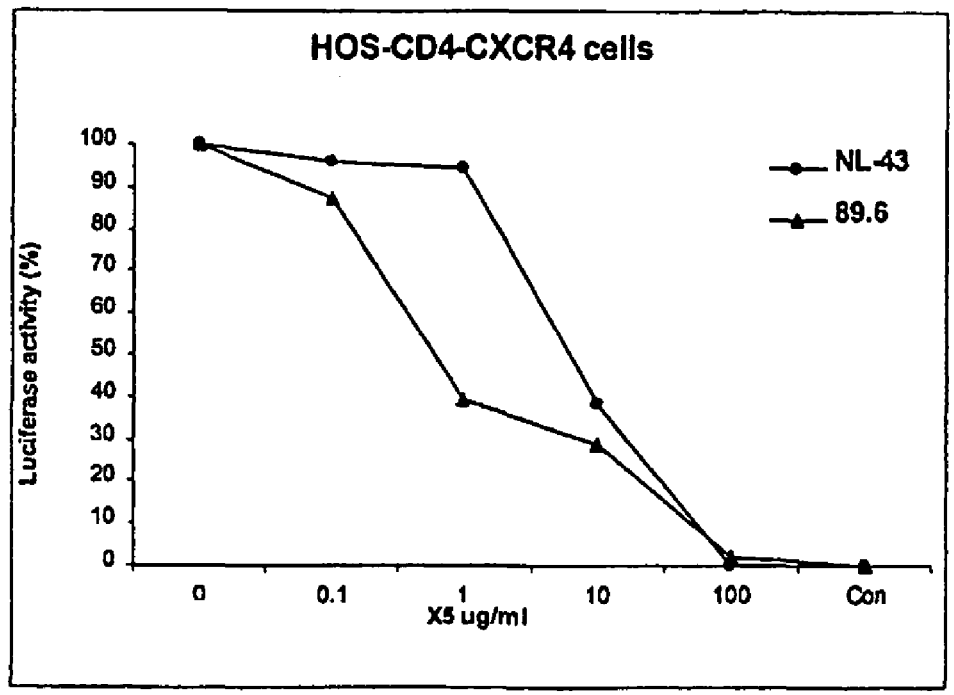

Inhibition of HIV-1 envelope glycoprotein-mediated cell fusion and entry. To find whether X5 inhibits HIV-1 Env-mediated fusion we used several assays. In a sCD4-induced fusion assay X5 inhibited almost completely sCD4-mediated fusion mediated by the dual tropic primary isolate Env 89.6 at very low (100 ng/ml) concentrations (FIG. 4). Similar results were obtained for several X4, R5 and X4R4 Envs (Table 1). Inhibition of fusion mediated by X4 Envs was somewhat less efficient compared to R5 Env-mediated fusion. Fusion mediated by cell-associated CD4 required on average 10-fold higher concentrations of X5. This may be related to the fact that cell-cell fusion is difficult to inhibit especially when the surface concentrations of CD4 and CCR5 (CXCR4) are high. X5 was able to neutralize several representative R5 (JRFL and Bal), X4 (NL4-3) and X4R5 (89.6) isolates of HIV-1 at concentrations in the range of 1 to 10 µg/ml (FIG. 5). These results indicate that X5 is a novel broadly neutralizing HIV-1 antibody which can be used as an efficient inhibitor of HIV-1 infections.

Table 1: Inhibition of sCD4-induced R5, X4, and R5-X4 Envs-mediated fusion by X5. The data are represented as % of control without X5; "-" denotes no fusion in the control. 293T cells were transfected by plasmids encoding various Envs. They were pre-incubated with sCD4 (1 ug/ml) and X5 (125 ng/ml) for 30 min at 37° C. and incubated with the target cells (SupT1 cells expressing CXCR4 and NIH 3T3 CD4.CCR5 cells) for 2 h at 37° C. Fusion was measured by the reporter gene fusion assay.

| Envs | NL4-3 | HXB2 | 89.6 | JRFL | ADA | Bal | SF162 |
|---|---|---|---|---|---|---|---|
| R5 | — | — | 99 | 98 | 96 | 96 | 100 |
| X4 | 83 | 71 | 79 | — | — | — | — |

Figure 6:
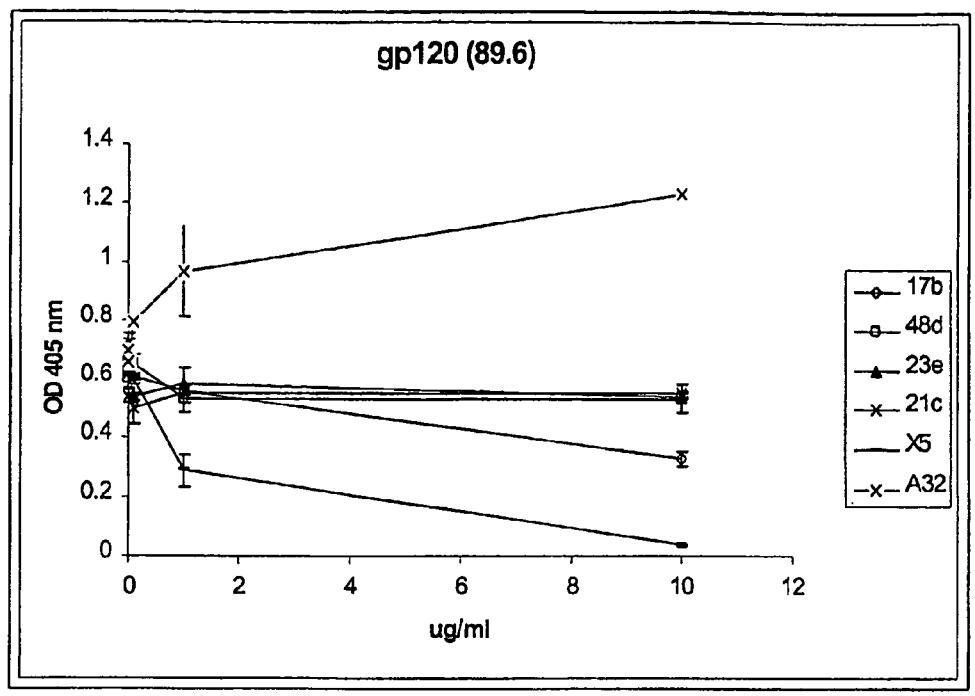
FIGS. 6A and 6B are graphs showing antibody competition assays for characterization of the X5 epitope. To characterize the X5 epitope, known CD4-inducible monoclonal antibodies (mAbs) were tested in an competition ELISA assay. Nunc-Immuno™ Maxisorp™ surface plates (Nalge Nunc International, Denmark) were coated with 100 ul of gp120 (FIG. 6A) or gp120+CD4 (FIG. 6B) (0.5 ug/ml each) in carbonated buffer, blocked with 4% milk in TBS. Fab X5 was biotinylated and a fixed concentration (0.5 ug/ml) was added to each well along with increasing concentrations (0, 0.01, 0.1, 1, 10 ug/ml) of indicated mAbs. Binding of biotinylated X5 was detected using streptavidin-HRP secondary Ab. Unbiotinylated X5 was also tested (at 0, 0.01, 0.1, 1, and 10 ug/ml) and more than 50% inhibition was detected at 1 ug/ml concentration.
Figure 6:
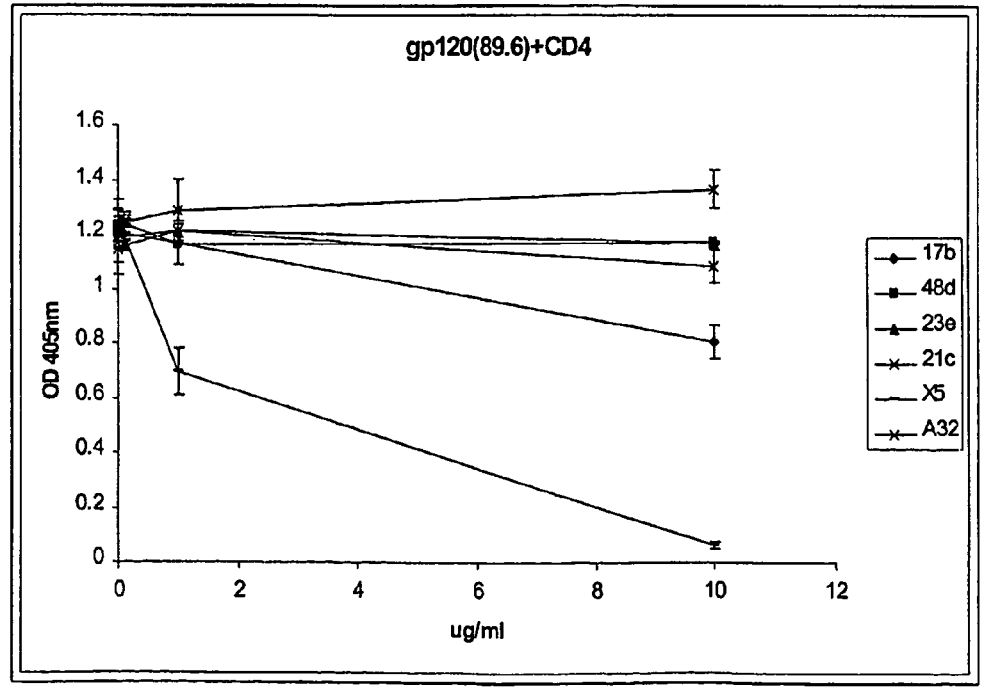

Characterization of the X5 epitope. To characterize the X5 binding site on gp120, we used several human monoclonal antibodies (gift of J. Robinson) against CD4-inducible epitopes. Two of these antibodies did not compete with X5 in the ELISA assay. Very low competition was observed with 17b at high concentrations (FIGS. 6A and 6B), suggesting slight epitope overlap or steric interference. Although we were not able to localize precisely the X5 epitope it appears that it is close to the gp41 association site with gp120, as indicated by the poorer binding of all gp140 Envs compared to gp120s. Studies of X5 competition with more antibodies with known epitopes and the X5 crystal structure in combination with the known gp120 core structure will facilitate determination of the precise epitope recognized by X5. The amino acid sequences of the X5 light and heavy chains are shown in FIGS. 7 and 8, respectively.

EXAMPLE II

Generation of X5 Antibody Sequence Variants with Increased Affinity for Env-CD4-co-Receptor Complexes The amino acid sequence of any antibody or antibody fragment of the invention may be varied in order to generate variant antibodies with equivalent or improved affinity for Env-CD4-co-receptor complexes. Such variant antibodies can be created and tested for their relative affinity using well-known methods and/or methods described herein. Such techniques are described, e.g., in Daugherty et al. ("Quantitative analysis of the effect of the mutation frequency on the affinity maturation of single chain Fv antibodies." *Proc. Natl. Acad. Sci. USA* 97(5):2029–34, 2000); Cherry et al. ("Directed evolution of a fungal peroxidase." *Nat. Biotechnol.* 17(4): 379–84, 1999); and Vartanian et al. ("Hypermutagenic PCR involving all four transitions and a sizeable proportion of transversions." *Nucleic Acids Res.* 24(14): 2627–31, 1996).

Random mutagenesis of the X5 antibody gene was used to identify X5 sequence variants with improved affinity for Env-CD4-CCR5 and Env-CD4 complexes. Two phage-X5 mutagenesis libraries, one expressing antibody X5 sequence variants as Fab fragments and the other expressing antibody X5 as scFv (single chain antibody) fragments, were constructed and panned sequentially against both complexes using methods similar to those described in Example I above. One Fab clone was selected from the X5-Fab mutagenesis library. The new X5-Fab clone, designated FabS, showed five-fold increased affinity for Env-CD4-CCR5 complex, compared to the original X5-Fab. The mutations were located in the joint region between the heavy chain variable region and the first constant domain (CH1), in which the alanine in the original X5 sequence was changed to proline and the serine in the original sequence was changed to glycine (SEQ ID NO: 11; FabS heavy chain sequence), as shown in FIG. 4. The nucleotide sequence encoding the light and heavy chains of FabS is set forth in SEQ ID NO: 12.

EXAMPLE III

Generation of Antibody Fusion Polypeptides Based on the X5 Antibody Sequence

Fusion proteins comprising antibody fragments and other functional domains which increase the efficacy of the antibody in treating, inhibiting, or preventing HIV infection are contemplated by the present invention. Such antibodies fusion proteins can be made using standard techniques that are well known in the art, and used in the methods of the invention for the treatment of and prophylaxis against infection by HIV. Below are several examples of fusion proteins based upon the X5 antibody fragment described in Example I above. Two basic types of fusion proteins are shown: those based upon single-chain antibody (ScFv) fragments, and those based upon Fab fragments. One of ordinary skill in the art will understand that any antibody or antibody fragment of the invention can be used to generate these and other types of fusion proteins.

The first example of such a fusion protein is a ScFvX5-CD4 fusion protein, i.e., a single-chain antibody (ScFv) fragment comprising a domain from the variable region of the X5 heavy chain (VH) and a domain from the variable region of the X5 light chain (VL), fused to fused to soluble CD4 (sCD4). The HV and LV domains are separated by a fifteen amino acid long flexible linker consisting of three repeats of the pentapeptide Gly-Gly-Gly-Gly-Ser (SEQ ID NO: 21), and the VL and sCD4 domains of the fusion protein are separated by a variable length flexible linker (e.g., containing 20, 30, or 40 amino acid residues) containing, e.g., four, six, or eight repeats of Gly-Gly-Gly-Gly-Ser. The components of this fusion protein, labeled a through e, are as follows. Although the example below shows the VH domain as being positioned amino-terminal to the VL domain (VH-Linker (L3)-VL-), one of ordinary skill in the art will readily recognize that the relative positions of the VH and VL domains can be swapped (e.g., VL-Linker (L3)-VH-) for all of the exemplary fusion protein constructs shown below.

A) ScFvX5-CD4 Fusion Protein

Construct: VH-Linker (L3)-VL-Linker(variable length)-sCD4 (a-b-c-d-e)

a) Variable Heavy Chain (VH) (SEQ ID NO: 14)

M A V Q L L E Q S G A E V K K P G S S V Q V S C K
A S G G T F S M Y G F N W V R Q A P G H G L E W M
G G I I P I F G T S N Y A Q K F R G R V T F T A D
Q A T S T A Y M E L T N L R S D D T A V Y Y C A R
D F G P D W E D G D S Y D G S G R G F F D F W G Q
G T L V T V S S b) Linker (L) (SEQ ID NO: 21)

(Gly$_4$Ser)×3 c) Variable Light Chain (VL) (SEQ ID NO: 15)

D I V L T Q S P G T L S L S A G E R A T L S C R A
S Q S V S S G S L A W Y Q Q K P G Q A P R L L I Y
G A S T R A T G I P D R F S G S G S G T D F T L T
I G R L E P E D L A V Y Y C Q Q Y G T S P Y T F G
Q G T K L E I K R T d) Linker (Variable length—20 or 30 or 40 a.a Long) (SEQ ID NO: 16, 17, or 18)

(Gly$_4$Ser)×4 or 6 or 8 e) sCD4 (Two Domain Soluble CD4) (SEQ ID NO: 19)

M N R G V P F R H L L L V L Q L A L L P A A T Q G
K K V V L G K K G D T V E L T C T A S Q K K S I Q
F H W K N S N Q I K I L G N Q G S F L T K G P S K
L N D R A D S R R S L W D Q G N F P L I I K N L K
I E D S D T Y I C E V E D Q K E E V Q L L V F G L
T A N S D T H L L Q G Q S L T L T L E S P P G S S
P S V Q C R S P R G K N I Q G G K T L S V S Q L E

-continued

L Q D S G T W T C T V L Q N Q K K V E F K I D I V
V L

Below is a second example of a fusion polypeptide that, in addition to the above components, also contains a synthetic peptide, T20, which corresponds to a peptide sequence found in HIV-1 gp41, and is a strong inhibitor of HIV-1 viral fusion (see, e.g., Lawless et al. *Biochemistry* 35:13697–13708, 1996).

B) ScFv-CD4-T20 Fusion Protein

Construct: VH-Linker (L3)-VL-Linker(variable length)-sCD4-L1-T20 (a-b-c-d-e-f-g)

This construct is identical to construct A above, but in addition, after sCD4, contains another linker and the T-20 peptide:

f) Linker (SEQ ID NO: 13)

(Gly$_4$Ser)×1 g) T-20Peptide (SEQ ID NO: 20)

Y T S L I H S L I E E S Q N Q Q E K N E Q E L L E
L D K W A S L W N W F

Below is an example of a fusion polypeptide containing an X5 Fab fragment, i.e., the X5 light chain fragment (VLCL) containing the variable region and the constant region, which is disulfide-bonded (represented below by "s-s") to the heavy chain fragment containing the variable region and the CH1 portion of the constant region (VHCH1). One of skill in the art will recognize that X5 Fabs can contain heavy and light chains containing PelB, OmpA, or other signal sequences that direct protein secretion, e.g., as set forth in SEQ ID NOs: 3 and 2, respectively, or can contain heavy and light chains that lack such signal sequences, e.g., as set forth in SEQ ID NOs:14 and 15, respectively.

The X5 Fab fusion protein shown below contains a soluble CD4 domain fused to the carboxy terminus of the X5 heavy chain. Constructs containing the sCD4 domain fused to the X5 light chain instead of the heavy chain may also be used.

C) Fab'-CD4 Fusion Protein

Construct: VLCL-s-s-VHCH1-Linker(variable length)-sCD4 a) X5 Fab Sequence (e.g., SEQ ID NOs: 3 Plus 2 or SEQ ID NOs: 14 Plus 15).

b) Linker (Variable length—20 or 30 or 40 a.a Long) (SEQ ID NO: 16, 17, or 18)

(Gly$_4$Ser)×4 or 6 or 8 c) sCD4 (Two Domain) (SEQ ID NO: 19)

M N R G V P F R H L L L V L Q L A L L P A A T Q G
K K V V L G K K G D T V E L T C T A S Q K K S I Q
F H W K N S N Q I K I L G N Q G S F L T K G P S K

-continued
LNDRADSRRSLWDQGNFPLIIKNLK

IEDSDTYICEVEDQKEEVQLLVFGL

TANSDTHLLQGQSLTLTLESPPGSS

PSVQCRSPRGKNIQGGKTLSVSQLE

LQDSGTWTCTVLQNQKKVEFKIDIV

VL

The fourth construct is the same as the X5 Fab construct above, except it also contains a T20 domain. The T20 domain, like the sCD4 domain, may also be fused to either the heavy chain or the light chain. The construct below shows the T20 domain directly connected to the sCD4 domain by a flexible linker; however, constructs with the sCD4 domain on one chain and the T20 domain on the other chain (connected to the remainder of the chain by a flexible linker) are also included in the present invention.

D) Fab'-CD4-T20 Fusion Protein

Construct: VLCL-s-s-VHCH1-Linker(variable length)-sCD4-L1-T20

This construct is the same as construct C above, but, in addition, after sCD4 contains:

d) Linker (SEQ ID NO: 13)

(Gly$_4$Ser)×1 e) T-20Peptide (SEQ ID NO: 20)

YTSLIHSLIEESQNQQEKNEQELLELDKWASLWNWF

SEQUENCES

Amino Acid Sequence of X5 Light Chain Including OmpA Signal (SEQ ID NO: 2)

MKKTAIAIAVALAGFATVAQAAELV

LTQSPGTLSLSAGERATLSCRASQS

VSSGSLAWYQQKPGQAPRLLIYGAS

TRATGIPDRFSGSGSGTDFTLTIGR

LEPEDLAVYYCQQYGTSPYTFGQGT

KLEIKRTVAAPSVFIFPPSDEQLKS

GTASVVCLLNNFYPREAKVQWKVDN

ALQSGNSQESVTEHDSRDSTYSLGS

TLTLSKADYEKHKVYACEVTHQGLS

SPVTKSFNRGEC

Amino Acid Sequence of X5 Heavy Chain, Including PelB Signal (SEQ ID NO: 3)

MKYLLPTAAAGLLLLAAQPAMAEVQ

LLEQSGAEVKKPGSSVQVSCKASGG

TFSMYGFNWVRQAPGHGLEWMGGII

PIFGTSNYAQKFRGRVTFTADQATS

TAYMELTNLRSDDTAVYYCARDFGP

DWEDGDSYDGSGRGFFDFWGQGTLV

TVSSASTKGPSVFPLAPSSKSTSGG

TAALGCLVKDYFPEPVTVSWNSGAL

TSGVHTFPAVLQSSGLYSLSSVVTV

PSSSLGTQTYICNVNHKPSNTKVDK

KVEPKSCDKTS

Nucleotide Sequence of X5 (SEQ ID NO: 4)

Length: 1539

```
  1 atgaaaaga cagctatcgc gattgcagtg gcactggctg gtttcgctac
 51 cgtggcccag gcggccgagc tcgtgttgac acagtctcca ggcaccctgt
101 ctttgtctgc aggggaaaga gccaccctct cctgcagggc cagtcagagt
151 gttagcagcg gctccttagc ctggtaccag cagaaacctg gtcaggctcc
201 caggctcctc atctacggtg catccaccag ggccactggc atcccagaca
251 ggttcagtgg cagtgggtct gggacagact tcactctcac aatcggcaga
301 ctggagcctg aagatctcgc agtatattac tgtcagcagt atggtacctc
351 accgtacact tttggccagg ggaccaaact ggagatcaaa cgaactgtgg
401 ctgcaccatc tgtcttcatc ttcccgccat ctgatgagca gttgaaatct
451 ggaactgcct ctgttgtgtg cctgctgaat aacttctatc ccagagaggc
501 caaagtacag tggaaggtgg ataacgccct ccaatcgggt aactcccagg
551 agagcgtcac agagcatgac agcagggaca gcacctacag cctcggcagc
601 accctgacgc tgagcaaagc agactacgag aaacacaaag tctacgcctg
651 cgaagtcacc catcagggcc tgagttcgcc cgtcacaaag agcttcaaca
```

```
 701 ggggagagtg ttaattctag ataattaatt aggaggaatt taaaatgaaa
 751 tacctattgc ctacggcagc cgctggattg ttattactcg ctgcccaacc
 801 agccatggcc gaggtgcagc tgctcgagca gtctggggct gaggtgaaga
 851 agcctgggtc ctcggtgcag gtctcctgca aggcctctgg aggcaccttc
 901 agcatgtatg gtttcaactg ggtgcgacag gcccctggac atggccttga
 951 gtggatggga gggatcatcc ctatctttgg tacatcaaac tacgcacaga
1001 agttccgggg cagagtcacg tttaccgcgg accaagccac gagcacagcc
1051 tacatggagc tgaccaacct gcgatctgac gacacggccg tctattattg
1101 tgcgagagat tttggccccg actgggaaga cggtgattcc tatgatggta
1151 gtggccgggg gttctttgac ttctgggggcc agggaaccct ggtcaccgtc
1201 tcctctgcct ccaccaaggg cccatcggtc ttccccctgg caccctcctc
1251 caagagcacc tctgggggca cagcggccct gggctgcctg gtcaaggact
1301 acttccccga accggtgacg gtgtcgtgga actcaggcgc cctgaccagc
1351 ggcgtgcaca ccttcccggc tgtcctacag tcctcaggac tctactccct
1401 cagcagcgtg gtgaccgtgc cctccagcag cttgggcacc cagacctaca
1451 tctgcaacgt gaatcacaag cccagcaaca ccaaggtgga caagaaagtt
1501 gagcccaaat cttgtgacaa aactagctaa ttaatttaa
```

Amino Acid Sequence of CDR3 Region of X5 Heavy Chain (SEQ ID NO: 5)

D F G P D W E D G D S Y D G S G R G F F D F

Amino Acid Sequence of CDR2 Region of X5 Heavy Chain (SEQ ID NO: 6)

G I I P I F G T S N Y A Q K F R G

Amino Acid Sequence of CDR1 Region of X5 Heavy Chain (SEQ ID NO: 7)

M Y G F N

Amino Acid Sequence of CDR3 Region of X5 Light Chain (SEQ ID NO: 8)

Q Q Y G T S P Y T F G Q G T K L E I K R

Amino Acid Sequence of CDR2 Region of X5 Light Chain (SEQ ID NO: 9)

G A S T R A T G I

Amino Acid Sequence of CDR1 Region of X5 Light Chain (SEQ ID NO: 10)

R A S Q S V S S G S L A W

Amino Acid Sequence of FabS Heavy Chain, Including PelB Signal (SEQ ID NO: 11)

M K Y L L P T A A A G L L L L A A Q P A M A E V Q

L L E Q S G A E V K K P G S S V Q V S C K A S G G

T F S M Y G F N W V R Q A P G H G L E W M G G I I

P I F G T S N Y A Q K F R G R V T F T A D Q A T S

T A Y M E L T N L R S D D T A V Y Y C A R D F G P

D W E D G D S Y D G S G R G F F D F W G Q G T L V

T V S S P G T K G P S V F P L A P S S K S T S G G

T A A L G C L V K D Y F P E P V T V S W N S G A L

T S G V H T F P A V L Q S S G L Y S L S S V V T V

P S S S L G T Q T Y I C N V N H K P S N T K V D K

K V E P K S C D K T S

Nucleotide Sequence of FabS (SEQ ID NO: 12)

```
   1 atgaaaaaga cagctatcgc gattgcagtg gcactggctg gtttcgctac
  51 cgtggcccag gcggccgagc tcgtgttgac acagtctcca ggcaccctgt
 101 ctttgtctgc aggggaaaga gccaccctct cctgcagggc cagtcagagt
 151 gttagcagcg gctccttagc ctggtaccag cagaaacctg gtcaggctcc
 201 caggctcctc atctacggtg catccaccag ggccactggc atcccagaca
 251 ggttcagtgg cagtgggtct gggacagact tcactctcac aatcggcaga
 301 ctggagcctg aagatctcgc agtatattac tgtcagcagt atggtacctc
 351 accgtacact tttggccagg ggaccaaact ggagatcaaa cgaactgtgg
 401 ctgcaccatc tgtcttcatc ttcccgccat ctgatgagca gttgaaatct
 451 ggaactgcct ctgttgtgtg cctgctgaat aacttctatc cagagaggc
 501 caaagtacag tggaaggtgg ataacgccct ccaatcgggt aactcccagg
 551 agagcgtcac agagcatgac agcagggaca gcacctacag cctcggcagc
 601 accctgacgc tgagcaaagc agactacgag aaacacaaag tctacgcctg
 651 cgaagtcacc catcagggcc tgagttcgcc cgtcacaaag agcttcaaca
 701 ggggagagtg ttaattctag ataattaatt aggaggaatt taaaatgaaa
 751 tacctattgc ctacggcagc cgctggattg ttattactcg ctgcccaacc
 801 agccatggcc gaggtgcagc tgctcgagca gtctggggct gaggtgaaga
 851 agcctgggtc ctcggtgcag gtctcctgca aggcctctgg aggcaccttc
 901 agcatgtatg gtttcaactg ggtgcgacag gcccctggac atggccttga
 951 gtggatggga gggatcatcc ctatctttgg tacatcaaac tacgcacaga
1001 agttccgggg cagagtcacg tttaccgcgg accaagccac gagcacagcc
1051 tacatggagc tgaccaacct gcgatctgac gacacggccg tctattattg
1101 tgcgagagat tttggccccg actgggaaga cggtgattcc tatgatggta
1151 gtggccgggg gttctttgac ttctggggcc agggaaccct ggtcaccgtc
1201 tcctctcccg ggaccaaggg cccatcggtc ttccccctgg caccctcctc
1251 caagagcacc tctgggggca gcggccct gggctgcctg gtcaaggact
1301 acttccccga accggtgacg gtgtcgtgga actcaggcgc cctgaccagc
1351 ggcgtgcaca ccttcccggc tgtcctacag tcctcaggac tctactccct
1401 cagcagcgtg gtgaccgtgc cctccagcag cttgggcacc cagacctaca
1451 tctgcaacgt gaatcacaag cccagcaaca ccaaggtgga caagaaagtt
1501 gagcccaaat cttgtgacaa aactagctaa ttaattttaa
```

INCORPORATION BY REFERENCE

All publications and patent applications mentioned in this specification are herein incorporated by reference to the same extent as if each independent publication or patent application was specifically and individually indicated to be incorporated by reference.

OTHER EMBODIMENTS

While the invention has been described in connection with specific embodiments thereof, it will be understood that it is capable of further modifications and this application is intended to cover any variations, uses, or adaptations of the invention following, in general, the principles of the invention and including such departures from the present disclosure come within known or customary practice within the art to which the invention pertains and may be applied to the essential features hereinbefore set forth, and follows in the scope of the appended claims.

---

SEQUENCE LISTING

<160> NUMBER OF SEQ ID NOS: 21

<210> SEQ ID NO 1
<211> LENGTH: 18
<212> TYPE: DNA
<213> ORGANISM: Artificial Sequence
<220> FEATURE:
<223> OTHER INFORMATION: Synthetic

<400> SEQUENCE: 1
gaagtagtcc ttgaccag                                                   18

<210> SEQ ID NO 2
<211> LENGTH: 237
<212> TYPE: PRT
<213> ORGANISM: Artificial Sequence
<220> FEATURE:
<223> OTHER INFORMATION: Synthetic

<400> SEQUENCE: 2

Met Lys Lys Thr Ala Ile Ala Ile Ala Val Ala Leu Ala Gly Phe Ala
1               5                   10                  15

Thr Val Ala Gln Ala Ala Glu Leu Val Leu Thr Gln Ser Pro Gly Thr
            20                  25                  30

Leu Ser Leu Ser Ala Gly Glu Arg Ala Thr Leu Ser Cys Arg Ala Ser
        35                  40                  45

Gln Ser Val Ser Ser Gly Ser Leu Ala Trp Tyr Gln Gln Lys Pro Gly
    50                  55                  60

Gln Ala Pro Arg Leu Leu Ile Tyr Gly Ala Ser Thr Arg Ala Thr Gly
65                  70                  75                  80

Ile Pro Asp Arg Phe Ser Gly Ser Gly Ser Gly Thr Asp Phe Thr Leu
                85                  90                  95

Thr Ile Gly Arg Leu Glu Pro Glu Asp Leu Ala Val Tyr Tyr Cys Gln
            100                 105                 110

Gln Tyr Gly Thr Ser Pro Tyr Thr Phe Gly Gln Gly Thr Lys Leu Glu
        115                 120                 125

Ile Lys Arg Thr Val Ala Ala Pro Ser Val Phe Ile Phe Pro Pro Ser
    130                 135                 140

```
Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
            165                 170                 175

Leu Gln Ser Gly Asn Ser Gln Glu Ser Val Thr Glu His Asp Ser Arg
            180                 185                 190

Asp Ser Thr Tyr Ser Leu Gly Ser Thr Leu Thr Leu Ser Lys Ala Asp
            195                 200                 205

Tyr Glu Lys His Lys Val Tyr Ala Cys Glu Val Thr His Gln Gly Leu
            210                 215                 220

Ser Ser Pro Val Thr Lys Ser Phe Asn Arg Gly Glu Cys
225                 230                 235

<210> SEQ ID NO 3
<211> LENGTH: 261
<212> TYPE: PRT
<213> ORGANISM: Artificial Sequence
<220> FEATURE:
<223> OTHER INFORMATION: Synthetic

<400> SEQUENCE: 3

Met Lys Tyr Leu Leu Pro Thr Ala Ala Ala Gly Leu Leu Leu Leu Ala
1               5                   10                  15

Ala Gln Pro Ala Met Ala Glu Val Gln Leu Leu Glu Gln Ser Gly Ala
            20                  25                  30

Glu Val Lys Lys Pro Gly Ser Ser Val Gln Val Ser Cys Lys Ala Ser
            35                  40                  45

Gly Gly Thr Phe Ser Met Tyr Gly Phe Asn Trp Val Arg Gln Ala Pro
50                  55                  60

Gly His Gly Leu Glu Trp Met Gly Gly Ile Ile Pro Ile Phe Gly Thr
65                  70                  75                  80

Ser Asn Tyr Ala Gln Lys Phe Arg Gly Arg Val Thr Phe Thr Ala Asp
            85                  90                  95

Gln Ala Thr Ser Thr Ala Tyr Met Glu Leu Thr Asn Leu Arg Ser Asp
            100                 105                 110

Asp Thr Ala Val Tyr Tyr Cys Ala Arg Asp Phe Gly Pro Asp Trp Glu
            115                 120                 125

Asp Gly Asp Ser Tyr Asp Gly Ser Gly Arg Gly Phe Phe Asp Phe Trp
            130                 135                 140

Gly Gln Gly Thr Leu Val Thr Val Ser Ser Ala Ser Thr Lys Gly Pro
145                 150                 155                 160

Ser Val Phe Pro Leu Ala Pro Ser Ser Lys Ser Thr Ser Gly Gly Thr
            165                 170                 175

Ala Ala Leu Gly Cys Leu Val Lys Asp Tyr Phe Pro Glu Pro Val Thr
            180                 185                 190

Val Ser Trp Asn Ser Gly Ala Leu Thr Ser Gly Val His Thr Phe Pro
            195                 200                 205

Ala Val Leu Gln Ser Ser Gly Leu Tyr Ser Leu Ser Ser Val Val Thr
            210                 215                 220

Val Pro Ser Ser Ser Leu Gly Thr Gln Thr Tyr Ile Cys Asn Val Asn
225                 230                 235                 240

His Lys Pro Ser Asn Thr Lys Val Asp Lys Lys Val Glu Pro Lys Ser
            245                 250                 255

Cys Asp Lys Thr Ser
            260
```

<210> SEQ ID NO 4
<211> LENGTH: 1539
<212> TYPE: DNA
<213> ORGANISM: Artificial Sequence
<220> FEATURE:
<223> OTHER INFORMATION: Synthetic

<400> SEQUENCE: 4

```
atgaaaaaga cagctatcgc gattgcagtg gcactggctg gtttcgctac cgtggcccag      60
gcggccgagc tcgtgttgac acagtctcca ggcaccctgt ctttgtctgc agggggaaaga   120
gccaccctct cctgcagggc cagtcagagt gttagcagcg ctccttagc ctggtaccag     180
cagaaacctg gtcaggctcc caggctcctc atctacggtg catccaccag ggccactggc    240
atcccagaca ggttcagtgg cagtgggtct gggacagact tcactctcac aatcggcaga    300
ctggagcctg aagatctcgc agtatattac tgtcagcagt atggtacctc accgtacact    360
tttggccagg ggaccaaact ggagatcaaa cgaactgtgg ctgcaccatc tgtcttcatc    420
ttcccgccat ctgatgagca gttgaaatct ggaactgcct ctgttgtgtg cctgctgaat    480
aacttctatc ccagagaggc caaagtacag tggaaggtgg ataacgccct ccaatcgggt    540
aactcccagg agagcgtcac agagcatgac agcagggaca gcacctacag cctcggcagc    600
accctgacgc tgagcaaagc agactacgag aaacacaaag tctacgcctg cgaagtcacc    660
catcagggcc tgagttcgcc cgtcacaaag agcttcaaca ggggagagtg ttaattctag    720
ataattaatt aggaggaatt taaaatgaaa tacctattgc ctacggcagc cgctggattg    780
ttattactcg ctgcccaacc agccatggcc gaggtgcagc tgctcgagca gtctggggct    840
gaggtgaaga gcctgggtc ctcggtgcag gtctcctgca aggcctctgg aggcaccttc    900
agcatgtatg gtttcaactg ggtgcgacag gcccctggac atggccttga gtggatggga    960
gggatcatcc ctatctttgg tacatcaaac tacgcacaga agttccgggg cagagtcacg   1020
tttaccgcgg accaagccac gagcacagcc tacatggagc tgaccaacct gcgatctgac   1080
gacacggccg tctattattg tgcgagagat tttggccccg actgggaaga cggtgattcc   1140
tatgatggta gtggccgggg gttctttgac ttctggggcc agggaaccct ggtcaccgtc   1200
tcctctgcct ccaccaaggg cccatcggtc ttccccctgg caccctcctc caagagcacc   1260
tctgggggca gcggccct gggctgcctg gtcaaggact acttccccga accggtgacg    1320
gtgtcgtgga actcaggcgc cctgaccagc ggcgtgcaca ccttcccggc tgtcctacag   1380
tcctcaggac tctactccct cagcagcgtg gtgaccgtgc cctccagcag cttgggcacc   1440
cagacctaca tctgcaacgt gaatcacaag cccagcaaca ccaaggtgga caagaaagtt   1500
gagcccaaat cttgtgacaa aactagctaa ttaatttaa                           1539
```

<210> SEQ ID NO 5
<211> LENGTH: 22
<212> TYPE: PRT
<213> ORGANISM: Artificial Sequence
<220> FEATURE:
<223> OTHER INFORMATION: Synthetic

<400> SEQUENCE: 5

Asp Phe Gly Pro Asp Trp Glu Asp Gly Asp Ser Tyr Asp Gly Ser Gly
1               5                   10                  15

Arg Gly Phe Phe Asp Phe
            20

```
<210> SEQ ID NO 6
<211> LENGTH: 17
<212> TYPE: PRT
<213> ORGANISM: Artificial Sequence
<220> FEATURE:
<223> OTHER INFORMATION: Synthetic

<400> SEQUENCE: 6

Gly Ile Ile Pro Ile Phe Gly Thr Ser Asn Tyr Ala Gln Lys Phe Arg
1               5                   10                  15

Gly

<210> SEQ ID NO 7
<211> LENGTH: 5
<212> TYPE: PRT
<213> ORGANISM: Artificial Sequence
<220> FEATURE:
<223> OTHER INFORMATION: Synthetic

<400> SEQUENCE: 7

Met Tyr Gly Phe Asn
1               5

<210> SEQ ID NO 8
<211> LENGTH: 20
<212> TYPE: PRT
<213> ORGANISM: Artificial Sequence
<220> FEATURE:
<223> OTHER INFORMATION: Synthetic

<400> SEQUENCE: 8

Gln Gln Tyr Gly Thr Ser Pro Tyr Thr Phe Gly Gln Gly Thr Lys Leu
1               5                   10                  15

Glu Ile Lys Arg
            20

<210> SEQ ID NO 9
<211> LENGTH: 9
<212> TYPE: PRT
<213> ORGANISM: Artificial Sequence
<220> FEATURE:
<223> OTHER INFORMATION: Synthetic

<400> SEQUENCE: 9

Gly Ala Ser Thr Arg Ala Thr Gly Ile
1               5

<210> SEQ ID NO 10
<211> LENGTH: 13
<212> TYPE: PRT
<213> ORGANISM: Artificial Sequence
<220> FEATURE:
<223> OTHER INFORMATION: Synthetic

<400> SEQUENCE: 10

Arg Ala Ser Gln Ser Val Ser Ser Gly Ser Leu Ala Trp
1               5                   10

<210> SEQ ID NO 11
<211> LENGTH: 261
<212> TYPE: PRT
<213> ORGANISM: Artificial Sequence
<220> FEATURE:
<223> OTHER INFORMATION: Synthetic

<400> SEQUENCE: 11
```

```
Met Lys Tyr Leu Leu Pro Thr Ala Ala Ala Gly Leu Leu Leu Ala
1               5                   10                  15

Ala Gln Pro Ala Met Ala Glu Val Gln Leu Leu Glu Gln Ser Gly Ala
            20                  25                  30

Glu Val Lys Lys Pro Gly Ser Ser Val Gln Val Ser Cys Lys Ala Ser
        35                  40                  45

Gly Gly Thr Phe Ser Met Tyr Gly Phe Asn Trp Val Arg Gln Ala Pro
    50                  55                  60

Gly His Gly Leu Glu Trp Met Gly Gly Ile Ile Pro Ile Phe Gly Thr
65                  70                  75                  80

Ser Asn Tyr Ala Gln Lys Phe Arg Gly Arg Val Thr Phe Thr Ala Asp
                85                  90                  95

Gln Ala Thr Ser Thr Ala Tyr Met Glu Leu Thr Asn Leu Arg Ser Asp
            100                 105                 110

Asp Thr Ala Val Tyr Tyr Cys Ala Arg Asp Phe Gly Pro Asp Trp Glu
        115                 120                 125

Asp Gly Asp Ser Tyr Asp Gly Ser Gly Arg Gly Phe Phe Asp Phe Trp
    130                 135                 140

Gly Gln Gly Thr Leu Val Thr Val Ser Ser Pro Gly Thr Lys Gly Pro
145                 150                 155                 160

Ser Val Phe Pro Leu Ala Pro Ser Ser Lys Ser Thr Ser Gly Gly Thr
                165                 170                 175

Ala Ala Leu Gly Cys Leu Val Lys Asp Tyr Phe Pro Glu Pro Val Thr
            180                 185                 190

Val Ser Trp Asn Ser Gly Ala Leu Thr Ser Gly Val His Thr Phe Pro
        195                 200                 205

Ala Val Leu Gln Ser Ser Gly Leu Tyr Ser Leu Ser Ser Val Val Thr
    210                 215                 220

Val Pro Ser Ser Ser Leu Gly Thr Gln Thr Tyr Ile Cys Asn Val Asn
225                 230                 235                 240

His Lys Pro Ser Asn Thr Lys Val Asp Lys Lys Val Glu Pro Lys Ser
                245                 250                 255

Cys Asp Lys Thr Ser
            260
```

<210> SEQ ID NO 12
<211> LENGTH: 1539
<212> TYPE: DNA
<213> ORGANISM: Artificial Sequence
<220> FEATURE:
<223> OTHER INFORMATION: Synthetic

<400> SEQUENCE: 12

```
atgaaaaaga cagctatcgc gattgcagtg gcactggctg gtttcgctac cgtggcccag      60
gcggccgagc tcgtgttgac acagtctcca ggcaccctgt ctttgtctgc agggggaaaga    120 gccaccctct cctgcagggc cagtcagagt gttagcagcg gctccttagc ctggtaccag    180
cagaaacctg gtcaggctcc caggctcctc atctacggtg catccaccag ggccactggc    240
atcccagaca ggttcagtgg cagtgggtct gggacagact tcactctcac aatcggcaga    300
ctggagcctg aagatctcgc agtatattac tgtcagcagt atggtacctc accgtacact    360
tttggccagg ggaccaaact ggagatcaaa cgaactgtgg ctgcaccatc tgtcttcatc    420
ttcccgccat ctgatgagca gttgaaatct ggaactgcct ctgttgtgtg cctgctgaat    480
aacttctatc ccagagaggc caaagtacag tggaaggtgg ataacgccct ccaatcgggt    540
```

```
aactcccagg agagcgtcac agagcatgac agcagggaca gcacctacag cctcggcagc    600
accctgacgc tgagcaaagc agactacgag aaacacaaag tctacgcctg cgaagtcacc    660
catcagggcc tgagttcgcc cgtcacaaag agcttcaaca ggggagagtg ttaattctag    720
ataattaatt aggaggaatt taaaatgaaa tacctattgc ctacggcagc cgctggattg    780
ttattactcg ctgcccaacc agccatggcc gaggtgcagc tgctcgagca gtctggggct    840
gaggtgaaga agcctgggtc ctcggtgcag gtctcctgca aggcctctgg aggcaccttc    900
agcatgtatg gtttcaactg ggtgcgacag gcccctggac atggccttga gtggatggga    960
gggatcatcc ctatctttgg tacatcaaac tacgcacaga agttccgggg cagagtcacg   1020
tttaccgcgg accaagccac gagcacagcc tacatggagc tgaccaacct gcgatctgac   1080
gacacggccg tctattattg tgcgagagat tttggccccg actgggaaga cggtgattcc   1140
tatgatggta gtggccgggg gttctttgac ttctgggcc agggaaccct ggtcaccgtc    1200
tcctctcccg ggaccaaggg cccatcggtc ttccccctgg cacctcctc caagagcacc    1260
tctggggca gcggccct gggctgcctg gtcaaggact acttccccga accggtgacg     1320
gtgtcgtgga actcaggcgc cctgaccagc ggcgtgcaca ccttcccggc tgtcctacag    1380
tcctcaggac tctactccct cagcagcgtg gtgaccgtgc cctccagcag cttgggcacc    1440
cagacctaca tctgcaacgt gaatcacaag cccagcaaca ccaaggtgga caagaaagtt    1500
gagcccaaat cttgtgacaa aactagctaa ttaatttaa                         1539
```

<210> SEQ ID NO 13
<211> LENGTH: 5
<212> TYPE: PRT
<213> ORGANISM: Artificial Sequence
<220> FEATURE:
<223> OTHER INFORMATION: Synthetic

<400> SEQUENCE: 13

Gly Gly Gly Gly Ser
1               5

<210> SEQ ID NO 14
<211> LENGTH: 133
<212> TYPE: PRT
<213> ORGANISM: Artificial Sequence
<220> FEATURE:
<223> OTHER INFORMATION: Synthetic

<400> SEQUENCE: 14

Met Ala Val Gln Leu Leu Glu Gln Ser Gly Ala Glu Val Lys Lys Pro
1               5                   10                  15

Gly Ser Ser Val Gln Val Ser Cys Lys Ala Ser Gly Gly Thr Phe Ser
                20                  25                  30

Met Tyr Gly Phe Asn Trp Val Arg Gln Ala Pro Gly His Gly Leu Glu
            35                  40                  45

Trp Met Gly Gly Ile Ile Pro Ile Phe Gly Thr Ser Asn Tyr Ala Gln
        50                  55                  60

Lys Phe Arg Gly Arg Val Thr Phe Thr Ala Asp Gln Ala Thr Ser Thr
65                  70                  75                  80

Ala Tyr Met Glu Leu Thr Asn Leu Arg Ser Asp Asp Thr Ala Val Tyr
                85                  90                  95

Tyr Cys Ala Arg Asp Phe Gly Pro Asp Trp Glu Asp Gly Asp Ser Tyr
                100                 105                 110

Asp Gly Ser Gly Arg Gly Phe Phe Asp Phe Trp Gly Gln Gly Thr Leu

```
            115                 120                 125
Val Thr Val Ser Ser
        130

<210> SEQ ID NO 15
<211> LENGTH: 110
<212> TYPE: PRT
<213> ORGANISM: Artificial Sequence
<220> FEATURE:
<223> OTHER INFORMATION: Synthetic

<400> SEQUENCE: 15

Asp Ile Val Leu Thr Gln Ser Pro Gly Thr Leu Ser Leu Ser Ala Gly
1               5                   10                  15

Glu Arg Ala Thr Leu Ser Cys Arg Ala Ser Gln Ser Val Ser Ser Gly
            20                  25                  30

Ser Leu Ala Trp Tyr Gln Gln Lys Pro Gly Gln Ala Pro Arg Leu Leu
        35                  40                  45

Ile Tyr Gly Ala Ser Thr Arg Ala Thr Gly Ile Pro Asp Arg Phe Ser
    50                  55                  60

Gly Ser Gly Ser Gly Thr Asp Phe Thr Leu Thr Ile Gly Arg Leu Glu
65                  70                  75                  80

Pro Glu Asp Leu Ala Val Tyr Tyr Cys Gln Gln Tyr Gly Thr Ser Pro
                85                  90                  95

Tyr Thr Phe Gly Gln Gly Thr Lys Leu Glu Ile Lys Arg Thr
            100                 105                 110

<210> SEQ ID NO 16
<211> LENGTH: 20
<212> TYPE: PRT
<213> ORGANISM: Artificial Sequence
<220> FEATURE:
<223> OTHER INFORMATION: Synthetic

<400> SEQUENCE: 16

Gly Gly Gly Gly Ser Gly Gly Gly Gly Ser Gly Gly Gly Gly Ser Gly
1               5                   10                  15

Gly Gly Gly Ser
        20

<210> SEQ ID NO 17
<211> LENGTH: 30
<212> TYPE: PRT
<213> ORGANISM: Artificial Sequence
<220> FEATURE:
<223> OTHER INFORMATION: Synthetic

<400> SEQUENCE: 17

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 18
<211> LENGTH: 40
<212> TYPE: PRT
<213> ORGANISM: Artificial Sequence
<220> FEATURE:
<223> OTHER INFORMATION: Synthetic

<400> SEQUENCE: 18

Gly Gly Gly Gly Ser Gly Gly Gly Gly Ser Gly Gly Gly Gly Ser Gly
```

```
                1               5                  10                 15
Gly Gly Gly Ser Gly Gly Gly Ser Gly Gly Gly Ser Gly Gly
                20                 25                 30

Gly Gly Ser Gly Gly Gly Gly Ser
        35              40

<210> SEQ ID NO 19
<211> LENGTH: 202
<212> TYPE: PRT
<213> ORGANISM: Artificial Sequence
<220> FEATURE:
<223> OTHER INFORMATION: Synthetic

<400> SEQUENCE: 19

Met Asn Arg Gly Val Pro Phe Arg His Leu Leu Leu Val Leu Gln Leu
 1               5                  10                 15

Ala Leu Leu Pro Ala Ala Thr Gln Gly Lys Lys Val Leu Gly Lys
                20                 25                 30

Lys Gly Asp Thr Val Glu Leu Thr Cys Thr Ala Ser Gln Lys Lys Ser
            35                 40                 45

Ile Gln Phe His Trp Lys Asn Ser Asn Gln Ile Lys Ile Leu Gly Asn
        50                 55                 60

Gln Gly Ser Phe Leu Thr Lys Gly Pro Ser Lys Leu Asn Asp Arg Ala
 65                 70                 75                 80

Asp Ser Arg Arg Ser Leu Trp Asp Gln Gly Asn Phe Pro Leu Ile Ile
                85                 90                 95

Lys Asn Leu Lys Ile Glu Asp Ser Asp Thr Tyr Ile Cys Glu Val Glu
                100                105                110

Asp Gln Lys Glu Glu Val Gln Leu Leu Val Phe Gly Leu Thr Ala Asn
            115                120                125

Ser Asp Thr His Leu Leu Gln Gly Gln Ser Leu Thr Leu Thr Leu Glu
        130                135                140

Ser Pro Pro Gly Ser Ser Pro Ser Val Gln Cys Arg Ser Pro Arg Gly
145                150                155                160

Lys Asn Ile Gln Gly Gly Lys Thr Leu Ser Val Ser Gln Leu Glu Leu
                165                170                175

Gln Asp Ser Gly Thr Trp Thr Cys Thr Val Leu Gln Asn Gln Lys Lys
            180                185                190

Val Glu Phe Lys Ile Asp Ile Val Val Leu
        195                200

<210> SEQ ID NO 20
<211> LENGTH: 36
<212> TYPE: PRT
<213> ORGANISM: Artificial Sequence
<220> FEATURE:
<223> OTHER INFORMATION: Synthetic

<400> SEQUENCE: 20

Tyr Thr Ser Leu Ile His Ser Leu Ile Glu Glu Ser Gln Asn Gln Gln
 1               5                  10                 15

Glu Lys Asn Glu Gln Glu Leu Leu Glu Leu Asp Lys Trp Ala Ser Leu
                20                 25                 30

Trp Asn Trp Phe
        35

<210> SEQ ID NO 21
<211> LENGTH: 15
```

```
<212> TYPE: PRT
<213> ORGANISM: Artificial Sequence
<220> FEATURE:
<223> OTHER INFORMATION: Synthetic

<400> SEQUENCE: 21

Gly Gly Gly Gly Ser Gly Gly Gly Gly Ser Gly Gly Gly Gly Ser
1               5                   10                  15
```

What is claimed is:

1. An isolated antibody or antibody fragment comprising SEQ ID NO: 5 or SEQ ID NO: 8.

2. The isolated antibody or antibody fragment of claim 1, wherein the antibody or antibody fragment specifically binds to a CD4-inducible epitope on HIV Env that is enhanced by binding a co-receptor for HIV.

3. The isolated antibody or antibody fragment of claim 2, wherein the epitope is on gp120.

4. The isolated antibody or antibody fragment of claim 1, wherein the isolated antibody or antibody fragment specifically binds to a complex comprising HIV gp120, CD4, and a co-receptor for HIV.

5. The isolated antibody or antibody fragment of claim 4, wherein the complex further comprises gp41.

6. The isolated antibody or antibody fragment of claim 2, wherein the HIV co-receptor is COR5 at CXCR4.

7. The isolated antibody or antibody fragment of claim 2, wherein the CD4-inducible epitope on HIV Env is a CD4-indncible epitope on HIV-1 Env.

8. The isolated antibody or antibody fragment of claim 1, wherein the isolated antibody or antibody fragment has broadly neutralizing activity against HIV-1.

9. The isolated antibody or antibody fragment of claim 1, wherein the isolated antibody or antibody fragment is monoclonal.

10. The isolated antibody or antibody fragment of claim 1, wherein the isolated antibody or antibody fragment is human or humanized.

11. The isolated antibody or antibody fragment of claim 1, wherein the isolated antibody or antibody fragment is isolated from a phage display library.

12. The isolated antibody or antibody fragment of claim 1, wherein the antibody or antibody fragment comprises SEQ ID NO: 3.

13. The isolated antibody or antibody fragment of claim 1, wherein the antibody or antibody fragment comprises SEQ ID NO: 2.

14. The isolated antibody or antibody fragment of claim 1, wherein the antibody or antibody fragment comprises SEQ ID NO: 3 and SEQ ID NO: 2.

15. The isolated antibody or antibody fragment of claim 1, wherein the isolated antibody or antibody fragment comprises SEQ ID NO: 5.

16. The isolated antibody or antibody fragment of claim 1, wherein the isolated antibody or antibody fragment comprises SEQ ID NO: 8.

17. The isolated antibody or antibody fragment of claim 1, wherein the antibody or antibody fragment further comprises a soluble CD4 domain.

18. The isolated antibody or antibody fragment of claim 17, wherein the antibody or antibody fragment further comprises peptide T20.

19. An isolated polypeptide comprising SEQ ID NO: 3.

20. An isolated polypeptide comprising SEQ ID NO: 2.

21. An isolated polypeptide comprising SEQ II) NO: 5.

22. An isolated polypeptide comprising SEQ ID NO: 8.

23. The isolated antibody or antibody fragment of claim 1, wherein the isolated antibody or antibody fragment comprises SEQ ID NO: 5 and SEQ ID NO: 8.

24. The isolated polypeptide of claim 20, wherein the polypeptide comprises SEQ ID NO: 2 and SEQ ID NO: 3.

25. The isolated polypeptida of claim 22, wherein the polypeptide comprises SEQ ID NO: 5 and SEQ ID NO: 8.

26. The isolated polypeptide of claim 25, wherein the polypeptide further comprises a soluble CD4 domain.

27. The isolated polypeptide of claim 24, wherein the polypeptide further comprises peptide T20.

* * * * *